(12) United States Patent
Rosenbloom

(10) Patent No.: US 7,166,435 B2
(45) Date of Patent: *Jan. 23, 2007

(54) COMPOSITIONS AND METHODS FOR REDUCING THE TRANSMISSIVITY OF ILLNESSES

(75) Inventor: Richard A. Rosenbloom, Elkins Park, PA (US)

(73) Assignee: The Quigley Corporation, Doylestown, PA (US)

( * ) Notice: Subject to any disclaimer, the term of this patent is extended or adjusted under 35 U.S.C. 154(b) by 91 days.

This patent is subject to a terminal disclaimer.

(21) Appl. No.: 11/012,764

(22) Filed: Dec. 14, 2004

(65) Prior Publication Data

US 2005/0147697 A1 Jul. 7, 2005

Related U.S. Application Data

(63) Continuation-in-part of application No. 10/359,889, filed on Feb. 6, 2003, which is a continuation-in-part of application No. PCT/US02/24794, filed on Aug. 6, 2002, which is a continuation-in-part of application No. 10/122,991, filed on Apr. 15, 2002, now Pat. No. 6,596,313, which is a continuation-in-part of application No. 09/923,090, filed on Aug. 6, 2001, now Pat. No. 6,592,896.

(51) Int. Cl.
    *C12Q 1/68* (2006.01)
(52) U.S. Cl. .............................. 435/6; 435/5
(58) Field of Classification Search .......... 435/5, 435/6

See application file for complete search history.

(56) References Cited

U.S. PATENT DOCUMENTS

| | | |
|---|---|---|
| 5,120,538 A | 6/1992 | Oei |
| 5,248,504 A | 9/1993 | Friedman |
| 5,385,734 A | 1/1995 | Friedman |
| 5,401,504 A | 3/1995 | Das et al. |
| 5,494,668 A | 2/1996 | Patwardhan |
| 5,707,630 A | 1/1998 | Morrow |
| 5,861,415 A | 1/1999 | Majeed et al. |
| 5,908,857 A | 6/1999 | Suzuki |
| 6,030,980 A | 2/2000 | Suzuki |
| 6,063,381 A | 5/2000 | Staggs |
| 6,174,542 B1 | 1/2001 | Hinton et al. |
| 6,261,607 B1 | 7/2001 | Newmark et al. |
| 6,274,177 B1 | 8/2001 | Wu et al. |
| 6,291,533 B1 | 9/2001 | Fleischner |
| 6,391,346 B1 | 5/2002 | Newmark et al. |
| 6,841,544 B1 | 1/2005 | Gelber et al. |

FOREIGN PATENT DOCUMENTS

| | | |
|---|---|---|
| CN | 1060012 A | 4/1992 |
| CN | 1116068 A | 2/1996 |
| CN | 1072823 A | 6/2003 |
| JP | 03228667 | 10/1991 |
| JP | 2000157209 A | 6/2000 |

OTHER PUBLICATIONS

Steer S A, Corbett J A, *The role and regulation of COX-2 during viral infection*, Viral Immunol. 2003;16(4):447-60 (Abstract Only).
Hentschel C, Eglau MC, Hahn EG, *Curcuma xanhorrhiza (Java turmeric) in clinical use*], Fortschr Med. Sep. 30, 1996;114(27):349-50 (Abstract Only).
Paster N, Juven B J, Harshemesh H, *Antimicrobial activity and inhibition of aflatoxin B1 formation by olive plant tissue constituents*, J. Appl. Bacteriol. Apr. 1988;64(4):293-7 (Abstract Only).
Cross, Karen J., et al, Mechanisms of cell by influenza virus, *Expert News in Molecular Medicine:* www.ermm.cbcu.cam.ac.uk. (01)00345-3h.htm (shortcode:txt001dsl): Aug. 6, 2001, 18 pgs.
Simonsen, L. et al., Preparing for this year's influenza season-(Brief Article), *Journal of Critical Illnesses*, Oct. 2001, pp. 1 & 2.
Prodigy Practical Support for Chemical Governance, Prodigy-Influenza, www.prodigy.nhs.uk/quidance.asp?gt-Influenza, Oct. 2003, 32 pgs.
Kaji, M., Neuraminidase inhibitor, anti-influenzal agent—mechanism of action, and how to use clinically, Nippon Rinsho. Nov. 2003;61(11):1975-9, PubMed, National Library of Medicine, PMID:14649441, Abstract, 1 pg.

(Continued)

*Primary Examiner*—Ali R. Salimi
(74) *Attorney, Agent, or Firm*—Knoble Yoshida & Dunleavy, LLC

(57) ABSTRACT

Methods for prophylactic and anti-transmissivity uses of an anti-microbial composition are disclosed. The methods comprise the step of administering to a mammal or a bird, an amount of a composition having a first ingredient obtainable from ginger; a second ingredient obtainable from green tea; an optional third ingredient obtainable from turmeric; and an acceptable carrier. When administered the composition is effective to reduce the incidence of contracting an illness or to prophylactically prevent transmission of an illness. Also disclosed are nasal and throat spray compositions for use in the methods of the invention.

30 Claims, No Drawings

OTHER PUBLICATIONS

Hayden, FG, et al., Use of the oral neuraminidase inhibitor oseltamivir in experimental human influenza: randomized controlled trials for prevention and treatment, JAMA. Oct. 6, 1999;282 (13):1240-6, PubMed, National Library of Medicine, PMID: 10517426, Abstract, 2 pgs.
botanical.com- A Modern Herbal, Horseradish- Herb Profile and Information, www.botanical.com/botanical/mgmh/h/horrad38.html, Published prior to Jun. 1, 2004, 4 pgs.
Kalsec-Aquaresins, Frequently asked questions, www. kalsec.com/products/aquresins_faq.cfm, p. 1 & 2. Aug. 18, 2004.
iHerb: HerbalGram The Journal of the American Botanical Council, Horseradish, www.herbalgram.org/iherb/expandedcommissione/he050, pp. 1-6. Oct. 20, 2004.
Nkoghe, D et al., Influenza: from vaccine prevention to antiviral therapy, Rev Med Liege. 2000;55(1):19-23, PubMed, National Library of Medicine, PMID: 10803033, Abstract, 1 pg.
Internet download, Prinz et al., "Saliva Tannin interactions", *J. Oral Rehabil,* Nov. 2000; 27(11) :991-4.
Internet download; Bacon et al., "Binding affinity of hydrolysable tannins to parotid saliva and to proline-rich proteins derives from it", *J. Agric Food Chem* Mar. 2000; 48(3) : 838-43.
Internet download; Lomniczi et al., "Inhibition of salivary secretion by lipopolysaccharide: possible role of prostaglandins", *Am J. Physiol Endocrinol Metabm* Aug. 2001.; 281.
Internet download; Brouet et al., "Curcumin an anti-tumour promoter and anti-inflammatory agent, inhibits induction of nitric oxide synthase in activated macrophages", *Biochem Biophys Res Commun*Jan. 17, 1995; 206.
Internet download, Rettori et al., "Control of salivary secretion by nitric oxide and its role in neuroimmunomodulation", *Ann NY Acad Sci* 2000; 917:258-67.
Internet download, Tjendraputra et al., "Effect of Ginger Constituents and Synthetic Analogues on Cyclooxygenase-2 Enzyme in Intact Cells", *Biorg Chem* Jun. 2001;29(3):156-163.
Internet article; ALS Survival Guide, Treatment for ALS; Feb. 5, 2002, pp. 1-15; lougehrigsdisease.net/als.
Park, "Sialorrhea, "The Srooling Patient"", Loyola University Health System, The Department of Otolaryngology Head & Neck Surgery, pp. 1-3, luhs.org/depts./otolaryn/P_peds.htm, Dec. 6, 2003.
Salzer, "Sialorrhea", Grand Rounds Archive at Baylor, The Bobby r. Alford Department of Otorhinolaryngology and Communicative Sciences, 1-3, Oct. 5, 1991.
Rettori et al., "Control of Salivary secretion by nitric oxide and its role in neuroimmunomodulation", *Ann NY Acad Sci* 2000;917:258-67.
Mier et al., "Treatment of Sialorrhea with glycopyrrolate A Double-blind, Dose-Ranging Study", *Pediatrics & Adolescent Medicine,* vol. 154, No. 12, Dec. 2000.
Internet page, "Where are your salivary glands?",.cfm American Academy of Otolaryngology—Head and Neck Surgery, entnet.org/healthinfo.throat/salivary 2003.
Legeza, et al., "Prostaglandins—their role in the mechanisms of the development of the primary reaction to radiation syndrome", *Radiats Biol Radioecol* Jan.-Feb. 1994;34(1):32-8.
Novozhenov, et al., "Changes in lipid peroxidation and the antioxidant system in patients with acute radiation sickness", *Voen Med Zh* Apr. 1993;(4):38-40, 80 Abstract.
Chaialo, et al., "Free-radical processes and blood antioxidant systems in the late period following acute radiation sickness", *Med Radiol (Mosk)* 1991;36(5):20-1 Abstract.
Legeza, et al., "Prostaglandins—their role in the mechanisms of the development of the primary reaction to radiation syndrome", *Radiats Biol Radioecol* Jan.-Feb. 1994;34(1):32-8.
Bazhan, "Lipid peroxidation and the antioxidant system in subjects exposed to the influence of extreme factors", *Lik Sprava* Dec. 1998;(8):47-50 Abstract.
Beckman, et al., "Radiation therapy impairs endothelium-dependent vasodilation in humans", *J Am Coll Cardiol* Mar. 1, 2001;37(3):761 Abstract.
Castillo, et al., "Antiosidant activity and radioprotective effects against chromosomal damage induced in vivo by X-rays of flavan-3-ols (Procyanidins) from grape seeds (Vitis vinifera): comparative study versus other phenolic and organic compounds", *J Agric Food Chem* May 2000;48(5):1738-45 Abstract.
Weiss, et al., "Radioprotection by antioxidants", *Ann N Y Acad Sci* 2000;899:44-60 Abstract.
Weiss, "Pharmacologic approaches to protection against radiation-induced lethality and other damage", *Environ Health Perspect* Dec. 1997; 105 Supp16:1473-8 Abstract.
Baraboi, et al., "Mechanism of the antistressor and antiradiation action of plant phenol compounds", *Ukr Biokhim Zh* Nov.-Dec. 1998;70(6):13-23 Abstract.
Wu, et al., "Synthesis and bio-activity of coumarin derivatives and studies on its relationships between activity and lipophilicity", *Yao Xue Xue Bao* 1993;28(4):266-72 Abstract.
Thresiamma, et al., "Protective effect of curcumin, ellagic acid and bixin on radiation induced toxicity", *Indian J Exp Biol* Sep. 1996;34(9):845-7 Abstract.
Deneke, "Thiol-based antioxidants", *Curr Top Cell Regul* 2000;36:151-80 Abstract.
Il'iuchenok, et al., "Pharmacological and radioprotective properties of some gamma-pyrone derivatives (flavanones and flavanols)", *Farmakol Toksikol* Sep.-Oct. 1975;38(5):607-12.
Kapitanov, et al., "Radiation-protective effectiveness of lycopene", *Radiats Biol Radioecol* May-Jun. 1994;34 (3):439-45 Abstract.
Beliaev, et al., "Modification of the body's resistance to acute ionizing radiationby synthetic beta-carotene", *Vopr Med Khim* Nov.-Dec. 1992;38(6):39-42 Abstract.
Chigareva, et al., "Radio-protective effect of sulfur-containing methylfuran derivatives and the role of thiols in its realization", *Radiobiologiia* Nov.-Dec. 1983;23(6):816-9 Abstract.
Samoilov, et al, "The radioprotective and antioxidant properties of solubilized alpha-tocopheraol acetate", *Eksp Klin Farmakol* Jul.-Aug. 1992;55(4):42-4 Abstract.
Kamat, et al., "Chlorophyllin as an effective antioxidant against membrane damage in vitor and ex vivo", *Biochim Biophys Acta* Sep. 27, 2000;1487(2-3):113-27 Abstract.
Kapitanov, et al., "Radiation-protective effectiveness of lycopene", *Radiats Biol Radioecol* May-Jun. 1994;34 (3):439-45 Abstract.
Internet download, "1001 Herbs for a Healthy Life" 2001, 1001 Herbs; pges 1 and 2.
Internet download, "Slippery Elm", MotherNature.com Health Encyclopedia, 1995-2000, MotherNature.com Inc., pp. 1 and 2.
Uma, et al., "Radiation protection by the ocimum flavonoids orientin and vicenin: mechanisms of action", *Radiat Res* Oct. 2000; 154(4):455-60 Abstract.
Moskalenko, et al., "The role of immunological mechanisms in the development of the late sequelae of nuclear disasters", *Lik Sprava* Jun. 1999;(4):3-8 Abstract.
Ovsiannikova, et al., "Efficacy of antioxidant preparations used for correction of impairment of oxidative homeostasis in Chernobyl liquidators", *Radiats Biol Radioecol* Mar.-Jun. 1999;39(2-3):318-21, Abstract.
Spector, et al., "Reduction of x-radiation mortality by cabbage and broccoli", *Proceedings of the Society of Experimental Biology and Medicine* 100:405-407 Citation, 1959.
Calloway, et al., "Further studies of the influence of diet on radiosensitivity of guinea pigs, with special reference to broccoli and alfalfa", *Journal of Nutrition* 19:340-348 Citation, 1962.
Chlorophyll as Therapy; 4:1-5; www.wheatgrass.com/book/chapter4.html, Copyright 1990.
Gamma Ray Irradiation; "Research finds chorella may offer protection against gamma-ray irradiation", www.health-books.com/PressRoom/Gamma.html; 1-2.
Antioxidants; "Also Known as: Free Radical Scavengers; Oxidative Scavengers", www.alternativehealth.com.au/antioxid.html; 1-9, 2003.
Goodman, "Protection from Heavy Metal and Radiation Poisoning", *Germanium-The health and life enhancer,* 5:1-8, 2003.
Afanas'ev, et al., "Chelating and free radical scavenging mechanisms of inhibitory action of rutin and quercetin in lipid peroxidation", *Biochem Pharmacol* Jun. 1, 1989;38(11):1763-9 Abstract.

Ishige, et al., "Flavonoids protect neuronalcells from oxidative stress by three distinct mechanisms", *Free Radic Biol Med* Feb. 15, 2001;30(4):433-46 Abstract.

Shobana, et al., "Antioxidant activity of selected Indian spices", *Prostaglandins Leukot Essent Fatty Acids* Feb. 2000;62(2):107-10 Abstract.

Tiukavkina, et al., "Dihydroquercetin—anew antioxidants and biologically active food additive", Vopr Pitan 1997;(6):12-5 Abstract.

Plumb, et al., "Antioxidants properties of flavonal glycosides from tea", *Redox Rep* 1999;4(1-2):13-6 Abstract.

Skaper, et al., "Quercetin protects cutaneous tissue-associated cell types including sensory neurons from oxidative stress induced by glutathione depletion: cooperative effects of ascorbic acid", *Free Radic Biol Med* 1997;22(4):669-78 Abstract.

Jones, et al., "Radioprotective effect of free radical scavenging enzymes", *J Otolaryngol* Oct. 1990:19(5):299-306 Abstract.

Boloor, et al., "Chlorophyllin as a protector of mitochondrial membranes against gamma-radiation and photosensitization", *Toxicology* Nov. 30, 2000;155(1-3):63-71 Abstract.

Kim, et al, "In vivo radioprotective activity of Panax ginseng and diethyldithiocarbamate", In Vivo Sep.-Oct. 1993;7(5):467-70 Abstract.

Rice-Evans, et al., "The relative antioxidant activities of plant-derived polyphenolic flavonoids", Free *Radic Res* 22:4:375-83 1995 Summary.

Gillis, "Panax ginseng pharmacology: a nitric oxide link", *Biochemical Pharmacology* 54:1-8 (1997) Summary.

Duke, et al., "Biological Activities of CURCUMINOIDS", Phytochemical and Ethnobotanical Database, 2003.

Robak, et al., "Bioactivity of flavonoids", *Pol J Pharmacol* Nov.-Dec. 1996;48(6):555-64 Abstract.

Bursel, et al., "Can protein kinase C inhibition and vitamin E prevent the development of diabetic vascular complications?", *Diabetes Res Clin Pract* Sep. 1999;45(2-3):169-82 Abstract.

Freedman, et al., "Select flavonoids and whole juice from purple grapes inhibit platelet functionand enhance nitric oxide release", *Circulation* Jun. 12, 2001;103(23):2792-8 Abstract.

Lin, et al., "Recent studies on the biofunctions and biotransformations of curcumin", *Biofactors* 2000;13(1-4):153-8 Abstract.

Isoherranen, et al., "Ultraviolet irradiation induces cyclooxygenase-2 expression in keratinocytes", *Br J Dermatol* Jun. 1999;140(6):1017-22 Abstract.

Duarte, et al., "Vasodilator effects of quercetin in isolated rat vascular smooth muscle", *Eur J Pharmacol* Aug. 1993 239:1-7 Abstract.

Giugliano, et al., "Oxidative stress and diabetic vascular complications", *Diabetes Care* Mar. 1996;19(3):257-67 Abstract.

On, et al., "Vitamin c prevents radiation-induced endothelium-dependent vasomotor dysfunction and de-endothelialization by inhibiting oxidative damage in the rat", *Clin Exp Pharmacol Physiol* Oct. 2001;28(10):816-21 Abstract.

Konopacka, et al., "Modifying effect of vitamins C, E and beta-carotene agaist gamma-ray-induced DNA damage in mouse cells", *Mutat Res* Sep. 11, 1998;417(203):85-94 Abstract.

Shope, "Radiation-induced skin injuries from fluoroscopy", Scientific Exhibit 060PH at the 81st Scientific Assembly and Annual Meting of the Radiological Society of North America, Nov. 26-Dec. 1, 1995, Radiology vol. 197(P) Supplement, P449 Abstract.

Noble-Adams, "Radiation-induced skin reactions. 2: Developement of a measurement tool", Br J Nurs Oct. 14-27, 1999;8(18):1208-11 Abstract.

Noble-Adams, "Radiation-induced skin reactions. 3: Evaluating in RISRAS", *Br J Nurs* Oct. 28-Nov. 10, 1999;8(19):1305-12 Abstract.

Cusma, et al., "Real-time measurement of radiation exposure to patients during diagnostic coronary angiography and percultaneous interventional procedures", *J Am Coll Cardiol* Feb. 1999;33(2):427-35 Abstract.

DOE Openness: Human Radiation Experiments: Roadmap to the Project, ACHRE Report, "How Does Radiation Affect Humans", pp. 1-5 at http://tis.eh.doe.gov/ohre/roadmap/achre/intro, 2003.

DOE Openness: Human Radiation Experiments: Roadmap to the Project, ACHRE Report, "What is Ionizing Radiation?", pp. 1-3 at http://tis.eh.doe.gov/ohre/roadmap/achre/intro, May 14, 2003.

Newall et al., "The control of oral secretions in bulbar ALS/MND", *J. Neurol Sci*, Aug. 1996 vol. 139 Supp;:43-44.

Morgan et al., "Topical treatment of radiation induced dermatitis with N-acetylcysteine (NAC)(Meeting Abstract) ", *Proc Annu Meet Am Assoc Cancer Res,* 1996; 37:A4142.

William F. Dial, *Cosmetic Dermatology*, "Topical Vitamin C May Help Protect Skin From UV Damage", Dec. 1991, pp. 34-35.

Bernard Idson, College of Pharmacology, University of Texas at Austin, Ultraviolet Irradiation Injury and Repair, Jan. 1992, pp. 22-24 and pp. 81-81.

Bisset et al., J. Soc. Cosmet. Chem., "Protective effect of a topically applied anti-oxidant plus an anti-inflammary agent against ultraviolet radiation-induced chronic skindamage in the hairless mouse", 43, Mar./Apr. 1992, pp. 85-92.

Darr et al., *British Journal of Dermatology*, "Topical vitamin C protects porcine skin from ultraviolet radiation-induced damage" (1992) 127, 247-253.

*Dermatology Times*, "New Aqueous Vitamin C blocks UV rays" 1991.

Fuchs et al., "Acute Effects of Near Ultraviolet and Visible Light on the Cutaneous Antioxidant Defense System"Oct. 3, 1988, pp. 739-744.

Vitamin E (Tocopherol) vs. Vitamin E Acetate, Roche, Jun. 1991.

Schmuth, et al., "Permeability barrier function of skin exposed to ionizing radiation" Arch Dermatol Aug. 2001; 137(8);1019-23.

Katiyar, et al., "Green tea polyphenol (-)-epigallocatechin-3-gallate treatment of human skin inhibits ultraviolet radiation-induced oxidative stress" Carcinogenesis Feb. 2001; 22(2):287-94.

Vitamin D-3 4000 I.U.—The Way Up (http://www.thewayup.com/products/0028.htm).

COMPOSITIONS AND METHODS FOR REDUCING THE TRANSMISSIVITY OF ILLNESSES

This application is a continuation-in-part of U.S. patent application Ser. No. 10/359,889 filed on Feb. 6, 2003, currently pending; which, in turn, is a continuation-in-part of International Patent Application No. PCT/US02/24794, filed on Aug. 6, 2002, designating the United States of America and published in English; which, in turn, is a continuation-in-part of U.S. patent application Ser. No. 10/122,991, filed on Apr. 15, 2002, now U.S. Pat. No. 6,596,313; which, in turn, is a continuation-in-part of U.S. patent application Ser. No. 09/923,090, filed on Aug. 6, 2001, now U.S. Pat. No. 6,592,896.

BACKGROUND OF THE INVENTION

1. Field of the Invention

The present invention relates the prophylactic use of a composition to reduce the incidence of contraction of illnesses caused by microbial organisms. More particularly, the present invention relates to methods for treating, reducing or preventing one or more symptoms or adverse effects of a microbial infection and to methods for reducing the infectivity or transmission of microbial infections.

2. Description of the Related Technology

Viral pathogenesis is the method by which viruses produce disease in the host. The pathogenesis of viruses centers on the mechanisms of viral injury to discrete populations of cells in particular organs to produce signs and symptoms of disease in a particular host.

To initiate an infection the virus must gain entry to the host cell. Entry routes are dependent on the virus and include the skin, eyes, respiratory, GI and urogenital tracts as well as the circulatory system. Some viruses localize their tissue injury in close proximity to their site of entry, particularly the viruses that infect the upper respiratory tract such as influenza, parainfluenza, rhinoviruses and coronavirus. Once the viral particle has invaded the cell, viral coded proteins direct the cell to replicate the viral genome and produce viral specific proteins. These proteins are assembled into complete virions along with the viral genome and released. In the case of enveloped viruses, the virions acquire a lipid membrane and will insert through this lipid membrane, viral specific glycoproteins. The enveloped virus families include the Herpesviridae, Retroviridae, Orthomyxoviridae, Paramyxoviridae, Flaviviridae, Togaviridae and Coronaviridae. The rhinoviruses are members of the Picornaviridae, which are not enveloped.

Viruses have evolved a number of mechanisms to enter a host cell and initiate infection. To fuse to the cell membrane, viruses have a membrane glycoprotein with membrane fusion activity. Many enveloped virus induce a receptor-mediated endocytosis after binding to the cell surface receptor, causing the cell to form an endosomal vesicle. Once inside the vesicle, the virus particle undergoes the uncoating process. This insures that the optimal pH for the viral genome is maintained and that the viral genome is protected from cellular nucleases.

Influenza viruses belong to the Orthomyxoviridae family of viruses and they are enveloped viruses containing negative-stranded RNA genomes with eight segments. The viral RNA encodes 10 viral specific proteins. Initiation of the infective cycle requires the binding of the viral envelop to the host cell-surface receptors, followed by receptor-mediated endocytosis and the fusion of the viral and endosomal membranes. The fusion process allows the release of the viral genome into the cytoplasm, where it can migrate to the nucleus where the viral genome initiates viral transcription and replication. The protein responsible for influenza receptor binding and membrane fusion is the hemagglutinin protein (HA or H antigen). For most strains, the HA protein is the most abundant glycoprotein on the surface of the virion. The HA protein is also the target for neutralizing antibodies. There are three serotypes of influenza viruses: A, B and C. Serotypes A and B cause the majority of clinical diseases. Influenza A occurs the most frequently, it is more virulent and it is responsible for the majority of epidemics and pandemics. Influenza A can be further subtyped based on the surface antigens HA and neuraminidase (N antigen) and the H and N antigens are the major antigenic determinants. Strains are also classified based on geographical location of the first isolate, serial number and year of isolation. Neuraminidase is an enzyme that facilitates the release of new viral particles from infected host cell. A third protein, M protein (matrix protein), is a membrane channel protein and is known as M2 in the A strains and NB in B strains. These surface viral membrane glycoproteins are the targets against which the immune system reacts.

Influenza viral particles attach to epithelial cells in the upper and lower respiratory track, where they invade the cell, release their genome and subjugate the host cell replication machinery to reproduce viral proteins and nucleic acid. Mature viral particles are released by lysis of the host cell. The resulting breaches in the respiratory epithelium results in an increase susceptibility to secondary infection. Influenza is transmitted primarily by respiratory secretions and these secretions are spread by coughing and sneezing. Influenza is also spread by direct contact when hands contaminated with the virus come in direct contact with the nasal passages or the eye. The incubation period is from 1 to 4 days and infected persons are generally infectious a day or two before symptoms appear and can remain infectious for 5 days after the onset of illness. Children and the immunocompromised shed virus for longer periods.

Influenza is prone to minor changes (i.e. point mutations) to one or both of the major surface antigens during replication. These changes are due in part to the lack of proofreading and error correction mechanisms in the virus transcriptional apparatus. The so-called antigenic drift is responsible for the seasonal epidemics because it can enable the virus to infect persons with only partial immunity from a prior exposure to the virus. Influenza A viruses are especially prone to antigenic drift. Major changes in the H and N antigens result in antigenic shift. Antigenic shift results in a new viral subtype and it can cause major epidemics and pandemics due to minimal populational immunity.

Influenza has been established as a serious human affliction that can cause localized epidemics and global pandemics of acute respiratory infections. Each year the influenza virus is responsible for 20,000 to 40,000 deaths and up to 300,000 hospitalization cases in the US. (Sandha and Mossad, Influenza in the Older Adult. Indications for the Use of Vaccine and Antiviral Therapy, Geriatrics 56:43–51, 2001, Oxford et al, In: Antigenic Variation, Ed. Craig & Scherf, Academic Press, London pp. 53–83, 2003). In the pandemic of 1918 it is widely believed that an excess of 40 million people died. Although children and younger adults experience more cases of infection, severe illness is more common in the elderly or immunocompromised individuals with chronic illnesses such as asthma, diabetes, kidney failure and heart disease. The annual epidemics run from November to March in the Northern Hemisphere and from April to September in the Southern Hemisphere.

Avian influenza is caused by type A strains of influenza virus. Avian influenza occurs throughout the world. Infected birds may display a wide range of symptoms, from a mild illness to a highly contagious fatal disease. The highly contagious disease is caused by an especially virulent strain of influenza virus. Infection by this strain is associated with a sudden onset of severe symptoms, such as a lack of energy, decreased egg production, soft shelled eggs, a swelling of the head, eyelids, etc., nasal discharge, coughing or diarrhea, resulting in death (WHO, 2004). At present, 15 subtypes have been identified that can infect birds but only H7, H5 and H9 subtypes are associated with outbreaks. The current Asian and British Columbia outbreaks are caused by a H5N1 and H7N3 strains, respectively. As discussed above, influenza viruses are a public health concern because these viruses lack a mechanism for proofreading nucleic acid replication as well as a repair system for correcting such errors. Thus, influenza viruses are especially prone to a high mutation rate during transcription. Additionally, influenza viruses are able to exchange or swap genetic material from other subtypes from different species, thus allowing subtypes to cross the species barrier that normally prevents the cross infection of species specific viruses from one species to another unrelated species. This species barrier normally prevents avian influenza virus strains from infecting humans, but occasionally new strains may have genetic material from both avian and human influenza virus strains. This exchange of genetic material occurs when there is a close proximity between humans and domestic poultry and swine. Swine may act as a reservoir for both human and avian strains. Thus swine act as a natural incubator for the emergence of new strains that can infect humans as well as avian species.

There are four antiviral drugs available in the US for the treatment of influenza: amantadine, rimatadine, zanamivir (Zanamivir (Relenza™) and Oseltamivir (Tamiflu™). Amantadine and rimatadine are effective only against influenza A. Amantadine, rimatadine and oseltamivir are approved for prophylaxis. Prophylaxis is indicated only for unvaccinated persons at high risk during an influenza outbreak. Antiviral agents have limited use due to poor tolerance and the occurrence of resistance. Presently, amantadine is the principal antiviral compound used against influenza infection, but its activity is restricted to influenza A viruses. The anti-neuraminidase inhibitors such as Zanamivir and Oseltamivir are a new class of antiviral agents licensed for use in the treatment of both influenza A and B infections (Carr et al., Influenza Virus Carrying Neuraminidase with Reduced Sensitivity to Oseltamiver Carboxylate has Altered Properties In Vitro and is Compromised for Infectivity and Replicative Ability In Vivo, Antiviral Res. 54:79–88, 2002). Therefore, the development of new and effective antiviral drugs against influenza A and B is of great clinical importance (Bamford, Neuraminidase Inhibitors as Potential Anti-Influenza Drugs, J. of Enzyme Inhibition, Review 10: 1–16, 1995).

Influenza vaccines are generally used before the onset of the influenza season and they are typically given to the segment of population that is considered to be at high risk. Vaccines come in several forms and they aim at preventing or at least lessening the symptoms of disease. Vaccines are given prior to exposure of the virus to generate neutralizing antibodies against the strain that is most likely to cause wide spread epidemics or pandemics. However, vaccinations can be costly and stocks of the vaccine can be depleted quickly. Also, vaccines may not contain the causative viral component. In other words, vaccine production depends upon estimating which strain will emerge as the dominant strain. Thus in any given year, there is only a limited protection against the various influenza strains. Furthermore, the typical method of providing a vaccine via injection is unpleasant to many. Prophylaxis treatments on the other hand, are used to prevent infection or lessen the severity of the disease post-exposure to the virus. Oseltamivir™ as well as zanamivir or Relenza™ (Glaxo Wellcome, second generation antiviral) are neuraminidase inhibitors that block the release of mature viral particles and thus prevent the infection of neighboring cells. Neuraminidase inhibitors lesson the symptoms of influenza infection and short the duration of the disease. Prophylaxis must be given within a 48-hour window of the onset of symptoms to be effective and there is a risk of resistant strains emerging.

Severe acute respiratory syndrome (SARS) is the first major new infectious disease of the 21st century. The first cases appeared in November of 2002 in Guangdong, China but it was only recognized as a new disease in March of 2003. The spread of the disease was accelerated by international air travel such that cases were reported in 22 countries. However, with modern communication technologies and a global collaborative effort the disease was contained within four months of being identified. The disease caused high morbidity and high mortality rates, with symptoms including a high fever, headache, myalgia and a dry cough. The mortality rate exceeded 60% in the over 60 age group (Peiris J S et al., 2003). SARS was identified as being caused by a new virus through various laboratory techniques involving virus propagation in tissue culture and electron microscopy studies. This was confirmed just days later when the complete genome sequence was determined indicating that it was a new Coronavirus that was responsible. Therefore the development of antimicrobial drugs for use against this type of infectious disease is of great importance.

Other microorganisms that cause illness include the gram-positive and gram-negative bacteria such as *Streptococcus, Staphylococcus, E. coli, Pseudomonas*, and *Haemophilus* as well as fungal infections including the yeast, *C. albicans*. While active infection with these microorganisms is primarily treated with antibiotics, some patients do not tolerate antibiotics well. Still others may wish to augment an antibiotic treatment with a treatment regiment that reduces or eliminates the symptoms of bacterial or fungal infection such as sore throat. Still others may want to prevent or lessen the severity of infections by one of these bacteria or fungi organisms by prophylactic treatment prior to, during or just after exposure.

Research interest has recently focused on various herbs, which contain potent antioxidant compounds that can provide significant protection against chronic diseases and have antimicrobial or anti-tumour activity. Antioxidant substances such as flavonoids can be found in a variety of herbs such as dandelion, ginger, green tea, and rosemary. It was recently reported that green-tea extract (GTE) inhibited the growth of influenza A and B viruses in Madin-Darby canine kidney (MDCK) cells and in another study, Epigallocatechin-3-gallate (EGCG), one of the components of green tea, inhibited the replication of HIV-1 (111B) and Bal HIV strains in peripheral blood lymphocytes. These substances have proven useful in the field treating various illnesses; however there has not been any progress in the creation of a prophylactic method for use with antioxidant substances.

Therefore, there exists a need in the field to provide a prophylactic method for the reduction of the incidence of contracting an illness caused by a microbial organism.

SUMMARY OF THE INVENTION

Accordingly, it is an object of certain embodiments of the invention to provide a method for reducing the incidence of contracting an illness caused by a microbial organism.

In the first aspect, the present invention relates to a method for the prophylactic use of an anti-microbial composition to reduce the incidence of contracting an illness. The method comprises the steps of administering to a mammal or a bird that has been, or will be, exposed to an illness caused by a microbe, an amount of an anti-microbial composition having a first ingredient obtainable from ginger; a second ingredient obtainable from green tea; and an acceptable carrier. The amount of anti-microbial composition is effective, when administered, to reduce the incidence of contracting the illness.

In a second aspect of the invention, a prophylactic anti-microbial composition having a first ingredient obtainable from ginger, a second ingredient obtainable from green tea; and an acceptable carrier is disclosed. The anti-microbial composition is effective, when administered as a nasal spray or as a throat spray to a mammal or a bird that has been, or will be, exposed to an illness caused by a microbe, to reduce the incidence of contracting said illness.

These and various other advantages and features of novelty that characterize the invention are pointed out with particularity in the claims annexed hereto and forming a part hereof. However, for a better understanding of the invention, its advantages, and the objects obtained by its use, reference should be made to the accompanying descriptive matter, in which there is described a preferred embodiment of the invention.

DETAILED DESCRIPTION OF THE PREFERRED EMBODIMENTS

In a first aspect, the present invention relates to a composition. The composition of the present invention includes ingredients that can be obtained from ginger, green tea and turmeric.

As used herein the term "flavors" includes both fruit and botanical flavors.

As used herein the term "sweeteners" includes sugars, for example, glucose, sucrose and fructose. Sugars also include high fructose corn syrup solids, invert sugar, sugar alcohols including sorbitol, and mixtures thereof. Artificial sweeteners are also included within the scope of the term, "sweetener."

As used herein, the term "acceptable" means a component that is suitable for use with humans and/or animals without undue adverse side effects (such as toxicity, irritation, and allergic responses), commensurate with a reasonable risk/benefit ratio.

Further, as used herein, the term "safe and effective amount" refers to the quantity of a component, which is sufficient to yield a desired therapeutic response without undue adverse side effects (such as toxicity, irritation, or allergic responses), commensurate with a reasonable risk/benefit ratio when used in the manner described herein.

The term "inhibiting" a microbe, as used herein, refers to reducing or preventing further growth of the microbe, or preventing the microbe from attaching to normal cells, and/or the elimination of some or all of the infectious particles from the human or animal being treated. Suitable methods for determining microbe inhibition are discussed in the examples.

The term "transmissivity" as used herein refers to the transfer of a microbe from one host to another.

All active compounds used in the present invention may be obtained from other sources, if available. Thus, the phrase "which can be obtained from" or the phrase "which may be obtained from" is meant to encompass compounds or compositions that are obtainable from turmeric, ginger, or green tea, and therefore encompasses synthetic forms of the same compounds and/or compositions as well as the same compounds and/or compositions obtained from other sources.

In a first embodiment, the composition of the present invention includes a first ingredient obtainable from ginger, and a second ingredient obtainable from green tea, in a safe and effective amount to provide one or more of the beneficial effects described herein.

The first ingredient of the composition of the present invention may be obtained from ginger (Zingiber officinale, also commonly called ginger root). Native to southern Asia, ginger is a 2- to 4-foot perennial that produces grass-like leaves up to a foot long and almost an inch wide. Ginger root, as it is called in the grocery store, actually consists of the underground stem of the plant, with its bark-like outer covering scraped off.

The active compounds of ginger which may be employed in the present invention include, but are not limited to, 1,8-cineole, 10-dehydrogingerdione, 10-gingerol, 6-gingerdione, 6-gingerol, 6-shogaol, 8-β-17-epoxy-λ-trans-12-ene-15,16-diol, 8-gingerol, 8-shogaol, 9-oxo-nerolidol, acetaldehyde, acetic acid, alanine, α-linolenic-acid, α-linolenic acid, α-phellandrene, α-piene, α-terpinene, α-terpineol, α-zingiberene, ar-curcumene, arginine, ascorbic acid, asparagine, β-bisabolol, β-carotene, β-elemene, β-eudesmol, β-ionone, β-myrcene, β-phellandrene, β-pinene, β-selinene, β-sesquiphellandrene, β-sitosterol, β-thujone, bornyl-acetate, boron, caffeic acid, calcium, camphene, camphor, capric acid, caprylic acid, capsaicin, caryophyllene, chavicol, chlorogenic acid, chromium, citral, citronellal, citronellal, cobalt, copper, cumene, curcumin, cystine, delphinidin, δ-cadinene, elemol, ethyl acetate, ethyl-myristate, farnesal, farnesene, ferulic acid, furfural, γ-aminobutyric acid, γ-terpinene, geranial, geraniol, geranyl-acetate, gingerenone, glutamic acid, glycine, hexahydrocurcumin, histidine, isogingerenone-B, isoleucine, kaempferol, lecithin, limonene, linoleic acid, magnesium, manganese, methionine, mufa, myrecene, myricetin, myristic acid, neral, nerol, nerolidol, niacin, nickel, oleic acid, oxalic acid, p-coumaric acid, p-cymene, p-hydroxy-benzoic acid, palmitic acid, pantothenic acid, paradol, patchoulic alcohol, phenylalanine, quercetin, riboflavin, selenium, shikimic-acid, terpinen-4-ol, thiamin, tryptophan, vanillic acid, vanillin, zinc, and zingerone. Also, mixtures of two or more of these active compounds may be employed.

The first ingredient of the composition of the present invention, which may be obtained from ginger, can be incorporated in the composition of the present invention in many different forms including extracts such as ginger powder extracts, ginger fluid extracts, ginger powder including ginger root powder, and one or more active compounds of ginger, parts of, or whole ginger plants, tinctures thereof, and mixtures thereof. Preferably, the first ingredient of the composition of the present invention is selected from ginger extract, and ginger root powder.

Each gram of the composition of the present invention preferably contains about 1 mg to about 150 mg of ginger root powder. Most preferably, each gram of the composition contains about 6 mg to about 110 mg of ginger root powder. These ranges use, as a baseline, the use of Ginger Root Powder, ex. Stryka Botanics in the ingested formulation and Ginger Extract K (Aquaresin® Ginger), ex. Kalsec®, Inc. of Kalamazoo, Mich. in the spray formulation.

The amounts of various ingredients are given herein in terms of one form of the ingredient, i.e. ginger root powder. If that ingredient is present in another form, then the amount to be employed is that amount which will provide the same amount of the one or more active compounds as the amount of that ingredient given herein. For example, if a tincture of ginger is employed, the amount of the tincture employed will be the amount that provides the same amounts of one or more active compounds as would be provided by the amounts of ginger root powder specified above. This applies to all ingredients for which the amounts are given herein for one particular form of that ingredient.

The second ingredient of the composition of the present invention may be obtained from green tea. The second ingredient obtained from green tea may have an antioxidant effect. Green tea is the dried leaves and leaf buds of the shrub *Camellia sinensis*. It is mainly produced in China and Japan. Dried tea leaves are composed mainly of phytochemicals known as polyphenols (about 36%), principally flavonols (including catechins), flavonoids, and flavondiols. The leaves also contain plant alkaloids (about 4%), including caffeine, theobromine and theophylline.

The pharmacological activities of green tea are mainly due to its active compounds. The active compounds of green tea useful in the present invention include, but are not limited to, flavonols, catechins, flavonoids, flavondiols, plant alkaloids, caffeine, theobromine, theophylline, phenolic acids, proteins, carbohydrates, and minerals.

The second ingredient which may be obtained from green tea, can be included in the composition in the form of green tea powder, green tea extracts such as green tea powder extracts, green tea fluid extracts, and one or more active compounds of green tea, part of, or whole green tea plants, green tea leaves, tinctures thereof, or mixtures thereof. Preferably, the second ingredient of the composition of the present invention is selected from green tea leaves, green tea powder and green tea extract. More preferably, the second ingredient of the composition of the present invention is green tea extract.

Each gram of the composition of the present invention preferably contains about 1 mg to about 20 mg of green tea extract. Most preferably, each gram of the composition contains about 4 mg to about 15 mg of green tea extract. These ranges use, as a baseline, the use of Green Tea, ex. Stryker Botanics in the ingested formulation and Green Tea Extract, ex. Phytoway, Inc., ChanSha, P.R. China, in the spray formulation.

The ingredients of the composition of the present invention, which may be obtained from ginger and green tea, and turmeric, may be used in the forms of turmeric powder, ginger powder and green tea powder, each of which may be ground from the rhizome of turmeric, ginger root and green tea leaves, respectively. For a particular active compound of ginger, green tea or turmeric, for which a synthetic route is known, the active compound may be synthesized. The plant extracts, if desired, may be prepared as described below. Alternatively, turmeric powder, ginger powder, green tea powder and/or one or more of the active compounds contained therein may be purchased from commercial sources such as the Kelsec®, Inc. of Kalamazoo, Mich.

The plant extracts, e.g., turmeric extract, ginger extract, green tea extract and horseradish extract that may be used in the compositions of the invention, may be produced using common extraction procedures. Alternatively, the extracts may be purchased from commercial sources such as the Kelsec®, Inc. of Kalamazoo, Mich.

The processes for the preparation of pharmacologically or biologically active plant extracts in a convenient, administrable dosage form from any of the plants mentioned above, are well known in the art.

The composition of the present invention may be used to treat viral infection, since the composition of the present invention has significant antimicrobial properties as demonstrated by the examples of this application. The composition of the present invention may also be used as a therapeutic composition to treat one or more symptoms of a viral infection, including sore throat, congestion, laryngitis, mucositis, and/or mucous membrane inflammation by administration to a patient suffering from one or more of these symptoms or ailments.

The composition of the present invention may also be employed to reduce the incidence of contracting an illness. In this application of the composition of the present invention, a safe and effective amount of the composition of the present invention is administered to a mammal or a bird that has been or will be exposed to an illness caused by a microbe, to reduce the incidence of contracting said illness, relative to a mammal or a bird that has been or will be exposed to an illness caused by a microbe to which the composition of the present invention has not been administered.

Preferably, the composition of the present invention may be formulated in any acceptable dosage form including, but not limited to, capsules, tablets, lozenges, troches, hard candies, powders, sprays, gels, elixirs, syrups, and suspensions or solutions. The composition of the present invention may also be administered in the form of a nutritional supplement, in which case the composition of the invention may be the nutritional supplement or may form a part of a nutritional supplement containing additional ingredients.

The composition of the present invention may also be formulated with an acceptable carrier. The acceptable carrier may include, but is not limited to: (a) carbohydrates including sweeteners, more preferably, fructose, sucrose, sugar, dextrose, starch, lactose, maltose, maltodextrins, corn syrup solids, honey solids, commercial tablet nutritional supplements including Emdex™, Mor-Rex™, Royal-T™, Di-Pac™, Sugar-Tab™, Sweet-Rex™, and New-Tab™; (b) sugar alcohols including mannitol, sorbitol and xylitol; and (c) various relatively insoluble excipients including dicalcium phosphate, calcium sulfate, calcium carbonate, microcrystalline cellulose and other tableting ingredients.

Lozenges, tablets, and troches in this invention may differ in shape, size and manufacturing technique. In the case of tablets, for oral use, the acceptable carrier may further include lactose and corn starch. Lubricating agents may also be added to the tablets, including, for example, magnesium stearate, sodium lauryl sulfate and talc. Tablets may also contain excipients such as sodium citrate, calcium carbonate and calcium phosphate. Disintegrants such as starch, alginic acid and complex silicates, may also be employed. Tablets may also include binding agents such as polyvinylpyrrolidone, gelatin, PEG-8000 and gum acacia.

In the case of lozenges for oral use, the common acceptable carrier may further include a binder such as PEG-8000. Preferably lozenges weigh about 0.1 to about 15 grams to provide a suitable dissolution rate when taken orally. More preferably, lozenges weigh about 1 to about 6 grams.

The production of lozenges is well known in the art and anyone with ordinary skill in the art can readily produce lozenges with the compositions of the present invention. The composition is preferably stored in an airtight container and in a cool dark place.

Tablets and troches can be manufactured using procedures known in the art with minor changes in the optional ingredients. Such changes are within the skill of the ordinary skilled artisan.

Alternatively, the composition of the present invention may be formulated in liquid form, such as syrups, mouthwashes or sprays, with a solvent or dispersant such as water, or other liquids and optionally in a pharmaceutically acceptable carrier, for repeated delivery of the composition to oral and oropharyngeal mucous membranes over a sustained period of time. Preferably, the treatment time is about 5 to 60 minutes, and more preferably about 20 to 30 minutes, so as to permit a prolonged contact of the composition with mouth and throat tissues. Alternatively, such formulations can be in a concentrated form suitable for dilution with water or other materials prior to use.

The composition may also be formulated in chewable forms, such as soft candy, gum drops, liquid filled candies, and chewing gum bases, or in the form of dental products, such as toothpastes and mouthwashes. In use, the chewable composition is preferably retained in the mouth over a sustained period of time of preferably about 5 to 60 minutes, and more preferably about 20 to 30 minutes. Dental products may be used in the ordinary manner of using such products.

The composition of the invention may be formulated in capsule form, with or without diluents. For capsules, useful diluents include lactose and dried corn starch. When suspensions are employed, emulsifying and/or suspending agents may be employed in the suspensions. In addition, solid compositions including one or more of the ingredients of the lozenges described above may be employed in soft and hard gelatin capsules.

The composition of the present invention may also be formulated into a nasal aerosol or inhalant composition. Such a composition may be prepared using well-known techniques. For these types of formulations, suitable carriers may include the following ingredients: saline with one or more preservatives, absorption promoters to enhance bioavailability, fluorocarbons, and/or conventional solubilizing or dispersion agents.

Other materials, which may optionally be included in the composition of the present invention, include resveratrol (trihydroxystilbene), inositol, other B-complex vitamins, and additional anti-inflammatories. Also, ingredients such as sweeteners, flavorants, coloring agents, dyes, preservatives, emulsifying agents, suspending agents, melting agents, excipients, demulcents and solvents or diluents such as water, ethanol, propylene glycol, glycerin and various combinations thereof, may be included in the composition of the present invention.

In an optional embodiment, the composition of the present invention includes one or more ingredients obtainable from turmeric, in a safe and effective amount to provide one or more of the beneficial effects described herein. Turmeric (*Curcuma longa*), or Haldi in Hindi, is used very widely as medicine as well as a common ingredient in Indian cooking. The rhizome of turmeric is used in medicine and food as a fine powder.

The yellow pigment of the rhizome of turmeric is composed of three compounds known as curcuminoids. The three curcuminoids are curcumin (diferuloylmethane), desmethoxycurcumin (hydroxycinnamoyl feruloylmethane), and bis-desmethoxycurcumin (dihydroxydicinnamoyl methane) (see Drug Analysis, Chromatography and Microscopy, p. 169, Ann Arbor Science Inc., 1973). The essential oils of turmeric (*Curcuma longa*) are primarily composed of the following compounds: d-camphor (about 1%), cyclo-isoprenemyrcene (about 85%), and p-tolylmethylcarbinol (about 5%), (see E. Gunther, The Essential Oil, pp. 123–4, Van Nostrand Co., 1955).

The ingredient of the composition of the present invention, obtained from turmeric, preferably includes curcuminoids, such as curcumin (diferuloylmethane), desmethoxycurcumin (hydroxycinnamoyl feruloylmethane), and bis-desmethoxycurcumin (dihydroxydicinnamoyl methane), and mixtures of two or more of these curcuminoids.

Methods for isolating curcuminoids from turmeric are known (see Janaki and Bose, An Improved Method for the Isolation of Curcumin From Turmeric, J. Indian Chem. Soc. 44:985, 1967). Alternatively, curcuminoids for use in the present invention can be prepared by synthetic methods.

The ingredient, which can be obtained from of turmeric, can be incorporated into the composition of the present invention in a variety of different forms. Those different forms preferably include extracts of turmeric such as turmeric powder extracts, turmeric fluid extracts, one or more the curcuminoid compounds, and turmeric powder, parts of, or whole plants of turmeric, tinctures thereof, and mixtures thereof. More preferably, the optional ingredient obtainable from turmeric is a turmeric extract.

When the ingredient obtainable from turmeric is used, each gram of the composition of the present invention preferably contains about 1 mg to about 20 mg of turmeric powder extract. Most preferably, each gram of the compositions contains about 6 mg to about 15 mg of turmeric powder extract. These ranges are based on the use of Turmeric Extract 95%, ex. Pharmline, Inc. in the ingested formulation and Turmeric Root Extract (Oleoresin Turmeric), ex. Kalsec®, Inc., Kalamazoo, Mich., in the spray formulation.

Also, the composition of the present invention may include one or more ingredients obtainable from horseradish root, in a safe and effective amount to provide one or more of the beneficial effects described herein.

The optional ingredient obtainable from horseradish root may include extracts from the *Cochlearia Armoracia*. Horseradish contains volatile oils that are similar to those found in mustard. These include glucosinolates (mustard oil glycosides), gluconasturtiin, and sinigrin, which yield allyl isothiocynate when broken down in the stomach.

Ethanol, propylene glycol and glycerin and various combinations thereof, may be optionally included in the composition of the present invention, up to about 10 percent by weight of the total as additional active ingredients. Most preferably, up to about 10 percent per total weight ethanol is added as an active ingredient. Even more preferable, 2.5 to 7 percent ethanol is added.

The optional sweeteners which may be used in the composition of the present invention include, but are not limited to, saccharin, aspartame, cyclamates, acesulfame K, neohesperidin dihydrochalcone, other super sweeteners, and mixtures thereof, which may be added to the carrier in amounts sufficiently low so as not to chemically interact with the main ingredients of the composition.

The optional flavorants which may be used in the composition of the present invention include, but are not limited to, peppermint, peppermint-menthol, eucalyptol, wintergreen, licorice, clove, cinnamon, spearmint, cherry, lemon, orange, lime, menthol and various combinations thereof.

Preferably, the main ingredients described above, that may be derived from ginger, green tea and, optionally, turmeric, make up from about 0.5 to about 90% by weight of the total composition. More preferably, the main ingredients will make up about 10 to about 70% by weight of the total composition. Most preferably, the main ingredients make up about 20 to about 40% by weight of the total composition.

The non-carrier ingredients of the composition, including the ingredients obtainable from turmeric, ginger, and green tea as discussed above, can be increased or decreased proportionally in the composition of the present invention depending on the amount of carrier used in the composition, without substantially affecting the effectiveness of the composition for its intended use.

Reducing or preventing transmission relates to preventing or reducing the spread of a microbe from one patient (infected) to another patient (non-infected). Some patients may be considered carriers of the infection. Carriers are individuals who actively shed microbes but do not suffer from an acute infection. These carriers may be said to be persistently (or chronically) infected with the microbe. In addition to the persistently infected shedder, other infective individuals may be those who are actively infected, and particularly those in the early or late stages of an acute infection. One aspect of the invention relates to administering to a mammal or a bird infected with a microbe, a composition of the present invention, to prevent the spread of the disease to other mammals or birds and/or reduce the symptoms of the disease in the infected mammal or bird.

Prophylactic treatment is aimed at a patient that will soon be exposed to a microbe or has recently been exposed to a microbe. Such prophylactic treatment may be effective either alone, or to augment a vaccine. Prophylactic treatment may also be used against microbes for which there is not yet a vaccine available. In the case of prophylactic treatment, the composition of the invention is administered to a patient that will be exposed to a microbe or has recently been exposed to a microbe for the purpose of reducing the incidence of active infection by the microbe in that patient.

In another aspect, the present invention relates to a method of reducing, treating or preventing of at least one symptom or adverse effect of viral infection by administering, to a patient infected with a virus, a composition of the present invention, including ingredients that can be obtained from ginger and green tea.

In the method, the patient may be a human, an in vitro cell system, or an animal. Preferably, the patient is a mammal, more preferably, a human. In the method, the virus that may be inhibited by administration of the composition of the present invention includes, among other viruses, rhinoviruses, influenza viruses, West Nile virus, herpes simplex virus, HIV-1, HIV-2, adenovirus, cornavirus, influenza virus, rubella virus, yellow fever virus and respiratory syncytial virus (RSV). In a preferred embodiment, the viruses that may be inhibited by administration of the composition include at least human rhinovirus 16, Herpes I Virus (HSV-1), Influenza A/Moscow/10/99, avian influenza A (H5N1), and B/Guangdong/120/00.

Alternatively, the patient may be a member of the bird (Avian) species, which includes the common commercial poultry birds: turkeys, ducks, geese and chickens, less commonly the ostrich as well as other bird species that are commonly kept as house pets, for example canaries and parrots. The composition may be administered by directly spraying the composition into the nasal passage of the bird or the composition may be administered by creating a mist through which the birds walk. Thus, the composition may be given prophylactically to act in a virucidal or virustatic manner. Alternatively, the composition may be used to reduce the transmissivity of the virus.

The symptoms, caused by a viral infection, that may be treated, reduced, or at least partially prevented by this method of the present invention, may include one or more of headache, joint pain, fever, cough, sneezing, muscle ache, running nose, dry mouth, dizziness, and other symptoms related to viral infection. In birds, these symptoms include a lack of energy, decreased egg production, soft shelled eggs, a swelling of the head, eyelids, etc., nasal discharge, coughing or diarrhea.

In the method, microorganisms that may be inhibited by administration of the composition of the present invention include gram-positive bacteria such as *Streptococcus, Staphylococcus*, gram-negative bacteria such as *E. coli, Pseudomonas, Haemophilus* and fungi such as *Histoplasma* and *Blastomycosis* and yeast such as *C. albicans* and *Crytococcus*.

The effective amount of the composition will vary depending on such factors as the patient being treated, the particular mode of administration, the activity of the particular active ingredients employed, the age, bodyweight, general health, sex and diet of the patient, time of administration, rate of excretion, the particular combination of ingredients employed, the total content of the main ingredient of the composition, and the severity of the illness or symptom. It is within the skill of the person of ordinary skill in the art to account for these factors.

The composition may be administered about 1 to about 15 times per day, as needed, more preferably, about 2 to about 12 times per day, as needed, or most preferably, about 6 to about 10 times per day, as needed. The composition of the present invention may be administered in any acceptable dosage form, as described above, including, but not limited to, tablets, capsules, lozenges, troches, hard candies, powders, oral sprays, nasal sprays, gels, elixirs, syrups, chewable compositions, dental products, suspensions, and solutions.

Each dosage of the composition contains a safe and effective amount of the composition of the present invention. An effective amount for each therapeutic administration contains a total of about 0.1 gram to about 1 gram of the ingredients, which may be obtained from ginger and green tea. More preferably, an effective amount of the composition for each therapeutic administration contains a total of about 0.2 gram to about 0.5 gram of the ingredients which may be obtained from ginger and green tea. The amounts of the various ingredients of the composition administered in accordance with the method of the present invention are the same as given above for the composition of the present invention.

Preferably, during each oral administration of the composition, the composition is held in the mouth for at least about 5 to about 60 minutes to enable the main ingredients of the composition to contact the mouth tissue or throat before it completely dissolves. More preferably, the composition is held in the mouth for at least about 15 to about 30 minutes.

When the composition is administered as a spray, the amounts each of the active ingredients may be reduced as the spray composition delivers the active ingredients more directly to the location where they are needed, as compared to a lozenge or capsule for example.

The following preferred ranges define compositions according to the invention that are suited for administration in a spray formulation according to the methods of the invention.

Each gram of the composition administered in a spray according to the methods of the present invention preferably contains about 1 mg to about 10 mg of aquaresin® ginger. Most preferably, each gram of the composition contains about 3 mg to about 7 mg of aquaresin® ginger.

Each gram of the composition administered in a spray according to the methods of the present invention preferably contains about 1 mg to about 20 mg of green tea leaf extract. Most preferably, each gram of the composition contains about 4 mg to about 15 mg of green tea leaf extract.

Each gram of an optional embodiment of a composition administered in a spray according to the methods of present invention preferably contains about 1 mg to about 12 mg of soluble oleoresin turmeric. Most preferably, each gram of the composition contains about 4 mg to about 9 mg of soluble oleoresin turmeric.

The invention will be further illustrated by the examples given below which are not to be construed as limiting the invention in any way. The scope of the invention is to be determined by the claims appended hereto.

EXAMPLE 1

A Composition of the Present Invention

A composition of the present invention formulated in the form of lozenges was prepared using the procedure described above. The ingredients of the lozenge are listed below:

| Ingredient | Amount |
| --- | --- |
| Sugar | 1 g |
| Slippery elm bark | 118 mg |
| Turmeric extract (5% curcumin) | 18 mg |
| Ginger root | 140 mg |
| Horseradish root | 70 mg |
| Green tea leaf extract (30% catechin and polyphenols) | 14 mg |

EXAMPLE 2

Treatment of Sore Throat

Each of seven patients, suffering from sore throats, ingested one lozenge formulated according to Example 1 every two hours by holding the lozenge in his or her mouth for about 15–30 minutes until the lozenge completely dissolved. No patient took more than 10 lozenges in any given day.

The patients that were treated reported complete relief from the symptoms of their sore throats after ingesting from 2 to 20 lozenges. It was also found that each lozenge can provide relief from a sore throat for up to 6 hours.

EXAMPLE 3

In Vitro Testing of Virucidal Activity of the Composition

The in vitro testing protocol for virucidal activity employed in this example uses human rhinovirus 16 (hereafter "HRV-16") as the target virus, and the MRC-5 cell line related to human tissues described by Jacobs et al., Characteristics of Human diploid MRC-5, Nature (London), 227:168–170 (1970) as the host cell for the HRV-16 viruses. Residual virus infectivity following incubation of the test substances with the virus was titrated on the MRC-5 cell line for rhinovirus growth by visually scoring the cytopathic effect (CPE) induced by virus replication through microscopic observation. More specifically, CPE was scored by observing ballooning/rounding cells in the MRC-5 culture.

To determine the virucidal activity, the composition of Example 1 (hereafter "Substance 1"), was employed at an initial dilution of 1/20 and then further diluted by serial dilutions in saline. The diluted compositions were incubated with HRV-16 for a set time period and then the reaction was terminated by adjustment to a neutral pH with cell infection media. The resultant solution was then titrated out on MRC-5 cells at a dilution of 1/10 across a testing plate to carry out the infection of the cells. Each plate housed a virus control, which contained only HRV-16 infected MRC-5 cells, and a cell control, which contained only uninfected MRC-cells.

The plates were further incubated for 4 days after the infection. Residual viral infectivity was measured using the assay discussed above. From the results shown in Tables 1–4, all of the controls on the plate worked well.

From the assay, it was concluded that Substance 1, at a 1/20 dilution, was effective in producing an HRV-16 viral log reduction of 1.50 ($-\log_{10}$ $TCID_{50}$) at the 1-minute incubation period. A 1/40 dilution of Substance 1 produced a log reduction of 1.00 ($-\log_{10}$ $TCID_{50}$) also at the 1-minute incubation period. After the 2-minute and 5-minute incubation periods, ½ log reductions in HRV-16 titer were achieved. Therefore, these results tend to indicate that a 1-minute contact time between Substance 1 and HRV-16 would produce the most effective viral titer reduction.

Table 1 shows the residual virus titers and log reductions of infectious Rhinovirus 16 on MRC-5 cells at one termination time point, of Substance 1 at different dilutions.

TABLE 1

| Dilutions | pH value of Substance 1 in Isotonic solution | pH value of terminated solution | Virus Control ($TCID_{50}$) | 1 Minute Incubation | |
| --- | --- | --- | --- | --- | --- |
| | | | | Residual Virus titer ($TCID_{50}$) | Log Reductions ($TCID_{50}$) |
| 1/20 | 5.03 | 7.73 | 3.80 | 2.30 | 1.50 |
| 1/40 | 5.13 | 7.77 | 3.80 | 3.30 | 0.50 |
| 1/80 | 4.98 | 7.83 | 3.80 | 3.80 | 0.00 |
| 1/160 | 4.98 | 7.73 | 3.80 | 3.80 | 0.00 |

Tables 2–4 show the results of a second trial on the residual virus titers and the log reductions of infectious HRV-16 on MRC-5 cells at three different termination time points, of Substance 1 at different dilutions.

TABLE 2

| | 1 Minute Incubation | | |
| --- | --- | --- | --- |
| Dilutions of Substance 1 | HRV-16 Control Titer (TCID$_{50}$) | Residual HRV-16 titer (TCID$_{50}$) | HRV-16 log Reductions (TCID$_{50}$) |
| 1/20 | 3.30 | 1.80 | 1.50 |
| 1/40 | 3.30 | 2.30 | 1.00 |
| 1/80 | 3.30 | 2.80 | 0.50 |
| 1/160 | 3.30 | 2.80 | 0.50 |
| 1/320 | 3.30 | 2.80 | 0.50 |

TABLE 3

| | 2 Minute Incubation | | |
| --- | --- | --- | --- |
| Dilutions of Substance 1 | HRV-16 Control Titer (TCID$_{50}$) | Residual HRV-16 titer (TCID$_{50}$) | HRV-16 log Reductions (TCID$_{50}$) |
| 1/20 | 3.30 | 2.80 | 0.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |

TABLE 4

| | 5 Minute Incubation | | |
| --- | --- | --- | --- |
| Dilutions of Substance 1 | HRV-16 Control Titer (TCID$_{50}$) | Residual HRV-16 titer (TCID$_{50}$) | HRV-16 log Reductions (TCID$_{50}$) |
| 1/20 | 3.30 | 2.80 | 0.50 |
| 1/40 | 3.30 | 2.80 | 0.50 |
| 1/80 | 3.30 | 3.30 | 0.00 |
| 1/160 | 3.30 | 2.80 | 0.50 |
| 1/320 | 3.30 | 2.80 | 0.50 |

In Tables 1–4, TCID50 = $-\log_{10}$ TCID$_{50}$.

Similar virucidal tests have been carried out for Substance 1 using other viruses, including Herpes I Virus (HSV-1) using Vero cells as the host cell, Influenza A/Moscow/10/99, and B/Guangdong/120/00 using MDCK cells as the host cell. The results on these virucidal tests are summarized below in Tables 5–13.

Tables 5–7 show the residual virus titers and log reductions of infectious HSV-1 on Vero cells at three different termination time points, of Substance 1 at different dilutions.

TABLE 5

| | 1 Minute Incubation | | |
| --- | --- | --- | --- |
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 2.80 | 1.00 |
| 1/320 | 3.80 | 2.80 | 1.00 |
| 1/640 | 3.80 | 2.80 | 1.00 |

TABLE 6

| | 2 Minute Incubation | | |
| --- | --- | --- | --- |
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

TABLE 7

| | 5 Minute Incubation | | |
| --- | --- | --- | --- |
| Dilutions of Substance 1 | HSV-1 Control Titer ($-\log_{10}$ TCID$_{50}$) | Residual HSV-1 titer ($-\log_{10}$ TCID$_{50}$) | HSV-1 log reductions ($-\log_{10}$ TCID$_{50}$) |
| 1/40 | 3.80 | 0.00 | 3.80 |
| 1/80 | 3.80 | 0.00 | 3.80 |
| 1/160 | 3.80 | 1.80 | 2.00 |
| 1/320 | 3.80 | 2.80 | 1.00 |
| 1/640 | 3.80 | 2.80 | 1.00 |

Tables 8–10 show the residual virus titers and log reductions of influenza A/Moscow/10/99 at three different termination time points, of Substance 1 at different dilutions.

TABLE 8

| | 1 Minute Incubation | | |
| --- | --- | --- | --- |
| Dilutions of Substance 1 | A/Moscow Virus Titer ($-\log_{10}$ TCID$_{50}$) | Residual A/Moscow titer ($-\log_{10}$ TCID$_{50}$) | A/Moscow log reductions ($-\log_{10}$ TCID$_{50}$) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 9

| | 2 Minute Incubation | | |
| --- | --- | --- | --- |
| Dilutions of Substance 1 | A/Moscow Virus Titer ($-\log_{10}$ TCID$_{50}$) | Residual A/Moscow titer ($-\log_{10}$ TCID$_{50}$) | A/Moscow log reductions ($-\log_{10}$ TCID$_{50}$) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 10

| | 5 Minute Incubation | | |
| --- | --- | --- | --- |
| Dilutions of Substance 1 | A/Moscow Virus Titer ($-\log_{10}$ TCID$_{50}$) | Residual A/Moscow titer ($-\log_{10}$ TCID$_{50}$) | A/Moscow log reductions ($-\log_{10}$ TCID$_{50}$) |
| 1/10 | 2.80 | 0.00 | 2.80 |
| 1/20 | 2.80 | 0.00 | 2.80 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 0.00 | 2.80 |

Tables 11–13 show the residual virus titers and log reductions of Influenza B/Guangdong/120/00 at three different termination time points, of Substance 1 at different dilutions.

TABLE 11

| | 1 Minute Incubation | | |
| --- | --- | --- | --- |
| Dilutions of Substance 1 | B/Guangdong Virus Titer ($-\log_{10}$ TCID$_{50}$) | Residual B/Guangdong titer ($-\log_{10}$ TCID$_{50}$) | B/Guangdong log reductions ($-\log_{10}$ TCID$_{50}$) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.30 | −0.50 |
| Citrate Buffer | 1.80 | 0.00 | 1.80 |

TABLE 12

| | 2 Minute Incubation | | |
| --- | --- | --- | --- |
| Dilutions of Substance 1 | B/Guangdong Virus Titer ($-\log_{10}$ TCID$_{50}$) | Residual B/Guangdong titer ($-\log_{10}$ TCID$_{50}$) | B/Guangdong log reductions ($-\log_{10}$ TCID$_{50}$) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.80 | −1.00 |
| Citrate Buffer | 1.80 | 0.00 | 1.80 |

TABLE 13

| | 5 Minute Incubation | | |
| --- | --- | --- | --- |
| Dilutions of Substance 1 | B/Guangdong Virus Titer ($-\log_{10}$ TCID$_{50}$) | Residual B/Guangdong titer ($-\log_{10}$ TCID$_{50}$) | B/Guangdong log reductions ($-\log_{10}$ TCID$_{50}$) |
| 1/10 | 1.80 | 0.00 | 1.80 |
| 1/20 | 1.80 | 0.00 | 1.80 |
| 1/40 | 1.80 | 1.80 | 0.00 |
| 1/80 | 1.80 | 1.80 | 0.00 |
| 1/160 | 2.30 | 1.80 | 0.50 |
| 1/320 | 2.30 | 1.80 | 0.50 |
| 1/640 | 1.80 | 2.80 | −1.00 |
| Citrate Buffer | 1.80 | 0.00 | 1.80 |

As can be seen from above results, Substance 1 is effective in inhibiting or exterminating influenza viruses and human rhinoviruses. As a result, Substance 1 should be effective in treating influenza and common colds.

EXAMPLE 4

In Vitro Testing of Virustatic Activity of the Composition

The in vitro testing protocol for virucidal activity employed in this example used human rhinovirus 16 (HRV-16) as the target virus, and the rhinovirus sensitive Hela cell line related to human tissues described by Conant et al., (Basis for a Numbering system. I. Hela cells for Propagation and Serologic Procedure, J. Immunol., 100:107–113, 1968) as the host cell for the HRV-16 virus.

Substance 1 was dissolved in infection media to the following dilutions: 1/20, 1/40, 1/80, 1/160 and 1/320. These dilutions were incubated on plates of MRC-5 cells for 30 minutes at 37° C. (5% $CO_2$). After the incubation period, each Substance 1 dilution with MRC-5 cells in a well of the plates was subjected to HRV-16 at a known titer of 2.30 ($-\log_{10}$ TCID$_{50}$). Each plate housed a virus control (the Hela cells infected with HRV-16 viruses and without Substance 1), a cell control (Hela cells only) and the test compound controls at the different dilutions (Hela cells with the test substance only). All the other samples on the plate contained the Hela cells infected with HRV-16 viruses and Substance 1 at different dilutions. The plates were further incubated for 4 days after infection.

Residual virus infectivity following incubation of Substance 1 with the virus was titrated on the Hela cell line for rhinovirus growth by measuring the cytopathic effect (CPE) induced by the virus using the following procedure.

The remaining viable Hela cells after incubation with Substance 1 were stained with crystal violet solution. Excess crystal violet was removed by washing and the crystal violet stained cells were solubilized using a mixture of methanol and acetic acid. The absorbance of the solution was then measured at 540 nm in an ELISA plate reader. The level of virus induced CPE was inversely proportional to the absorbance.

The results generated from the crystal violet assay enabled the toxic concentration and the effective concentration of Substance 1 to be determined by fitting an equation, $y=mx+c$, wherein x corresponds to the dilution of Substance 1 and y corresponds to percentage of toxicity of Substance 1 to the cells. From this equation, the TC$_{50}$ (concentration at which Substance 1 indicates 50% toxicity to the cells) is at a 1/571 dilution of Substance 1.

This result correlates well with the percentage of cell survivors at various dilution of Substance 1, which was also measured using the crystal violet assay, as shown in Table 14 below.

TABLE 14

| Dilution of Substance 1 without Virus | % Cell Survivors |
| --- | --- |
| 1/320 | 89.7 |
| 1/160 | 94.6 |
| 1/80 | 97.6 |
| 1/40 | 109.3 |
| 1/20 | 168.2 |

Using the same equation, wherein x still corresponds to the dilution of Substance 1 and y corresponds to the percent efficacy of Substance 1 in the presence of the virus, the $EC_{50}$ (concentration at which the test substance indicates 50% efficacy in the presence of virus) was determined to be at a 1/91 dilution of Substance 1. This result correlates well with the percentage of viable cells at various dilutions of Substance 1 measured using the crystal violet assay, as shown in Table 15 below.

TABLE 15

| Substance 1 dilution and Virus | % Viable Cells |
|---|---|
| 1/320 + HRV-16 | 79.3 |
| 1/160 + HRV-16 | 62.3 |
| 1/80 + HRV-16 | 39.0 |
| 1/40 + HRV-16 | 15.9 |
| 1/20 + HRV-16 | −220.0 |

In Tables 14 and 15, % Cell Survivors=(Compound only/Cell only)×100; and % Viable Cells=(Cell only−Compound+Virus)/(Cell only−Virus only)×100.

"Compound only" denotes the measurement results for the wells containing only Hela cells and Substance 1 at a predetermined dilution.

"Cell only" denotes the measurement results for the wells containing only uninfected Hela cells.

"Compound+Virus" denotes the measurement results for the wells containing the Hela cells infected with HRV-16 viruses and Substance 1 at a predetermined dilution.

"Virus Only" denotes the measurement results for the wells containing the Hela cells infected with HRV-16 only.

EXAMPLE 5

An Antimicrobial Lozenge of the Present Invention

An antimicrobial lozenge was made according to the formulation set forth below.

| 1) | Dextrose | 865.0 mg |
|---|---|---|
| 2) | Slippery Elm Bark | 150.0 mg |
| 3) | Stearic Acid | 75.0 mg |
| 4) | Ginger Root | 105.0 mg (Children) or 140.0 mg (Adult) |
| 5) | Horseradish Root | 70.0 mg |
| 6) | Honey Natural Flavor | 40.0 mg |
| 7) | Turmeric Extract (5% Curcumin) | 15.0 mg |
| 8) | Green Tea Leaf Extract (36% C & P) | 14.0 mg |
| 9) | Silicon Dioxide | 14.0 mg |
| 10) | Magnesium Stearate | 12.0 mg |
| 11) | Sucralose/Splenda | 4.0 mg |
| Tablet Weight: | | 1364.0 mg |

Note: C & P as used herein means "catechols and phenols."

EXAMPLE 6

An Antimicrobial Spray of the Present Invention

An antimicrobial spray was made according to the formulation set forth below.

| (1) | Slippery Elm Bark Extract | 18.52 mg |
|---|---|---|
| (2) | Oleoresin Turmeric, Soluble (~8.5% Curcumin) | 8.82 mg |
| (3) | Aquaresin ® Ginger | 7.0 mg |
| (4) | Horseradish Flavor WONF | 0.62 mg |
| (5) | Green Tea Leaf PE 50% Colorimetric | 14.0 mg |
| (6) | Honey Natural Flavor | 40.0 mg |
| (7) | Ethanol (95%) @ 5% | 68.2 mg |
| (8) | Glycerine | 603.42 mg |
| (9) | Distilled Water | 603.42 mg |
| Total Weight: | | 1364.0 mg |

EXAMPLE 7

In Vitro Testing of Antimicrobial Lozenge

The antimicrobial lozenge of Example 5 was tested for virucidal and virustatic activity against infection of MDCK cells with influenza viruses of the strains A/NewCaledonia/20/99 (H1N1), A/Panama/2007/99 (H3N2), and B/Guangdong/120/00.

In determining virucidal activity, the lozenge was tested at dilutions of 1/10, 1/20, 1/40, 1/80, 1/160, 1/320, and 1/640. The lozenge was diluted with saline isotonic solution (Normasol). Each dilution was tested at termination points of 1, 2, and 5 minutes after the lozenge came in contact with each virus. The reaction was terminated with 1.8 ml of 0% FBS cell media.

The log reductions in this example are reported as $-\log_{10} TCID_{50}$ and were calculated using the Karber equation.

TABLE 16

The residual virus titers and log reductions of infectious A/New Caledonia/20/99 (H1N1) virus after the 1-minute termination time point at different dilutions.

| | 1 Minute Incubation | | |
|---|---|---|---|
| Dilution | A/New Caledonia Virus titer ($-\log_{10} TCID_{50}$) | Residual Influenza titer ($-\log_{10} TCID_{50}$) | Virus log reductions ($-\log_{10} TCID_{50}$) |
| 1/10 | 2.80 | 0.00 | 2.80 |
| 1/20 | 2.80 | 2.30 | 0.50 |
| 1/40 | 2.80 | 1.80 | 1.00 |
| 1/80 | 2.80 | 2.30 | 0.50 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 17

The residual virus titers and log reductions of infectious A/New Caledonia/20/99 (H1N1) virus after the 2-minute termination time point at different dilutions.

| | 2 Minute Incubation | | |
|---|---|---|---|
| Dilution | A/New Caledonia Virus Titer ($-\log_{10} TCID_{50}$) | Residual Influenza titer ($-\log_{10} TCID_{50}$) | Virus log reductions ($-\log_{10} TCID_{50}$) |
| 1/10 | 2.80 | 0.00 | 2.80 |
| 1/20 | 2.80 | 1.80 | 1.00 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 18

The residual virus titers and log reductions of infectious A/New Caledonia/20/99 (H1N1) virus after the 5-minute termination time point at different dilutions.

| Dilution | A/New Caledonia Virus titer ($-\log_{10}$ $TCID_{50}$) | 5 Minute Incubation Residual Influenza titer ($-\log_{10}$ $TCID_{50}$) | Virus log reductions ($-\log_{10}$ $TCID_{50}$) |
|---|---|---|---|
| 1/10 | 2.80 | 0.00 | 2.80 |
| 1/20 | 2.80 | 1.80 | 1.00 |
| 1/40 | 2.80 | 1.80 | 1.00 |
| 1/80 | 2.80 | 1.80 | 1.00 |
| 1/160 | 2.80 | 1.80 | 1.00 |
| 1/320 | 2.80 | 1.80 | 1.00 |
| 1/640 | 2.80 | 1.80 | 1.00 |
| Citrate Buffer | 2.80 | 1.80 | 1.00 |

TABLE 19

The residual virus titers and log reductions of infectious A/Panama/2007/99 (H3N2) virus after the 1-minute termination time point at different dilutions.

| Dilution | A/Panama Virus Titer ($-\log_{10}$ $TCID_{50}$) | 1 Minute Incubation Residual Influenza titer ($-\log_{10}$ $TCID_{50}$) | Virus log reductions ($-\log_{10}$ $TCID_{50}$) |
|---|---|---|---|
| 1/10 | 4.80 | 3.80 | 1.00 |
| 1/20 | 4.80 | 3.80 | 1.00 |
| 1/40 | 4.80 | 4.80 | 0.00 |
| 1/80 | 4.80 | 4.30 | 0.50 |
| 1/160 | 4.80 | 4.80 | 0.00 |
| 1/320 | 4.80 | 4.80 | 0.00 |
| 1/640 | 4.80 | 4.80 | 0.00 |
| Citrate Buffer | 4.80 | 0.00 | 4.80 |

TABLE 20

The residual virus titers and log reductions of infectious A/Panama/2007/99 (H3N2) virus after the 2-minute termination time point at different dilutions.

| Dilution | A/Panama Virus Titer ($-\log_{10}$ $TCID_{50}$) | 2 Minute Incubation Residual Influenza titer ($-\log_{10}$ $TCID_{50}$) | Virus log reductions ($-\log_{10}$ $TCID_{50}$) |
|---|---|---|---|
| 1/10 | 4.80 | 3.80 | 1.00 |
| 1/20 | 4.80 | 4.30 | 0.50 |
| 1/40 | 4.80 | 4.80 | 0.00 |
| 1/80 | 4.80 | 4.30 | 0.50 |
| 1/160 | 4.80 | 4.80 | 0.00 |
| 1/320 | 4.80 | 4.80 | 0.00 |
| 1/640 | 4.80 | 4.80 | 0.00 |
| Citrate Buffer | 4.80 | 2.30 | 2.50 |

TABLE 21

The residual virus titers and log reductions of infectious A/Panama/2007/99 (H3N2) virus after the 5-minute termination time point at different dilutions.

| Dilution | A/Panama Virus titer ($-\log_{10}$ $TCID_{50}$) | 5 Minute Incubation Residual Influenza titer ($-\log_{10}$ $TCID_{50}$) | Virus log reductions ($-\log_{10}$ $TCID_{50}$) |
|---|---|---|---|
| 1/10 | 4.80 | 3.80 | 1.00 |
| 1/20 | 4.80 | 4.30 | 0.50 |
| 1/40 | 4.80 | 4.80 | 0.00 |
| 1/80 | 4.80 | 4.80 | 0.00 |
| 1/160 | 4.80 | 4.80 | 0.00 |
| 1/320 | 4.80 | 4.80 | 0.00 |
| 1/640 | 4.80 | 4.80 | 0.00 |
| Citrate Buffer | 4.80 | 2.80 | 2.00 |

TABLE 22

The residual virus titers and log reductions of infectious B/Guangdong/120/00 virus after the 1-minute termination time point at different dilutions.

| Dilution | B/Guangdong Virus Titer ($-\log_{10}$ $TCID_{50}$) | 1 Minute Incubation Residual Influenza titer ($-\log_{10}$ $TCID_{50}$) | Virus log reductions ($-\log_{10}$ $TCID_{50}$) |
|---|---|---|---|
| 1/10 | 3.30 | 1.30 | 2.00 |
| 1/20 | 3.30 | 1.80 | 1.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |
| 1/640 | 3.30 | 2.80 | 0.50 |
| Citrate Buffer | 3.30 | 0.00 | 3.30 |

TABLE 23

The residual virus titers and log reductions of infectious B/Guangdong/120/00 virus after the 2-minute termination time point at different dilutions.

| Dilution | B/Guangdong Virus Titer ($-\log_{10}$ $TCID_{50}$) | 2 Minute Incubation Residual Influenza titer ($-\log_{10}$ $TCID_{50}$) | Virus log reductions ($-\log_{10}$ $TCID_{50}$) |
|---|---|---|---|
| 1/10 | 3.30 | 1.80 | 1.50 |
| 1/20 | 3.30 | 1.80 | 1.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 2.80 | 0.50 |
| 1/640 | 3.30 | 2.80 | 0.50 |
| Citrate Buffer | 3.30 | 0.00 | 3.30 |

TABLE 24

The residual virus titers and log reductions of infectious B/Guangdong/120/00 virus after the 5-minute termination time point at different dilutions.

| | 5 Minute Incubation | | |
|---|---|---|---|
| Dilution | B/Guangdong Virus titer ($-\log_{10} TCID_{50}$) | Residual Influenza titer ($-\log_{10} TCID_{50}$) | Virus log reductions ($-\log_{10} TCID_{50}$) |
| 1/10 | 3.30 | 1.80 | 1.50 |
| 1/20 | 3.30 | 1.80 | 1.50 |
| 1/40 | 3.30 | 2.80 | 0.50 |
| 1/80 | 3.30 | 2.80 | 0.50 |
| 1/160 | 3.30 | 2.80 | 0.50 |
| 1/320 | 3.30 | 3.30 | 0.00 |
| 1/640 | 3.30 | 1.80 | 1.50 |
| Citrate Buffer | 3.30 | 0.00 | 3.30 |

In the viricidal assay, a known titer of Influenza virus was used as the virus control; this control underwent the same procedures as the test compound, QR-435. The Influenza titer on all plates was consistent with a virus control titer greater than 2.5 ($-\log_{10} TCID_{50}$).

EXAMPLE 8

In Vivo Testing of Antimicrobial Spray

The ferret is an established animal model for the study of influenza infection (Boyd and Beeson, 1975; Chen et al., Induction and Relief of nasal Congestion in Ferrets Infected with Influenza, Int. J. Exp. Pathol. 76:55–64, 1995; Scheiblauer et al., Pathogenicity of Influenza A/Seal/Mass/1/80 Virus Mutants for Mammalian Species, Arch. Virol. 140:341–8, 1995; Sweet and Smith, Pathogenicity of Influenza Virus, Microbiol. Rev. 44:303–30, 1980; Toms et al., The relation of Pyrexia and Nasal Inflammatory Response to Virus Levels in Nasal Washings of Ferrets Infected with Influenza Viruses of differing Virulence, Br. J. Exp. Pathol., 58:444–58, 1997; Webster et al., Protection of Ferrets Against Influenza Challenge with a DNA Vaccine to haemagglutinin, Vaccine 12: 1495–8, 1994). The ferret model has previously been used to determine the efficacy of influenza vaccines (Fenton et al., 1981; Webster et al., 1994). Transmission studies that utilized the ferret animal model have not only demonstrated donor to recipient spread of influenza virus, but also the effects of mutations on the virulence of the virus (Herlocher et al., Ferrets as a Transmission Model for Influenza: Sequence changes on the HA1 of type A (H3N2) Virus, J. of Infect. Diseases 184:542–46, 2001; Herlocher et al., Influenza virus carrying an R292K Mutation in the Neuraminidase Gene is not Transmitted in Ferrets, Antimicrobial Res. 54:99–111, 2002).

Five minutes before being infected with an influenza virus of the strain A/Sydney/5/97 (H3N2), four groups of six naïve ferrets received intranasal doses of experimental or control compositions. The negative control group received a phosphate buffer solution (PBS) placebo. The positive control group was treated with Tamiflu™ (oseltamivir phosphate, available from Roche Laboratories of Nutley, N.J.). One experimental group was treated with the nasal spray of Example 6, and the other was treated with a similar nasal spray that did not include green tea extract. After the initial challenge, the ferrets were dosed with their assigned composition twice a day.

The ferrets in the PBS treated control group exhibited all the symptoms typical of ferrets infected with influenza A, including weight loss, fever, increased inflammatory cell counts, and virus shedding on the first day after infection. The ferrets in the Tamiflu™ treated control group experienced no weight loss, no virus shedding, a reduction in inflammatory cell count rise, and no febrile illness.

Both the test formulation of Example 6 and the similar nasal spray that did not include green tea extract provided a low-level intermediary reduction in inflammatory cell count, prevented development of a febrile illness, and delayed virus shedding in a manner that may indicate virus suppression. Ferrets treated with nasal spray according to Example 6, however, also showed some lessening of weight loss. Ferrets treated with nasal spray according to Example 6 were more active than ferrets treated with the Tamiflu™.

EXAMPLE 9

In Vivo Transmissivity and Prophylaxis Testing

The properties of a nasal spray, QR-435, were tested. The formulation for QR-435 was as follows:

QR-435 Formulation

| Oleoresin Turmeric | 0.0308 weight percent |
|---|---|
| Aquaresin ® Ginger | 0.0326 weight percent |
| Horseradish Oil #58 | 0.00300 weight percent |
| Green Tea PE 030725 | 0.0220 weight percent |
| Glycerin | 2.3368 weight percent |
| Deionized Water | 97.5749 weight percent |

The study explored the effectiveness of the intranasal application by spray to prevent viral transmission to animals living in close proximity to an infected animal when the infected animal is treated and the provision of prophylaxis to uninfected animals.

Fifty ferrets (albino or Fitch, from Highgate Farms, Lincolnshire, GB) approximately 6–8 months old, 700–1200 g in weight were divided into 6 groups after electronic tagging, as shown in Table 25. Health scores were measured from day 0 to day 6 and the appropriate animal was placed under anesthesia for intranasal infection, with 0.25 ml per nostril, with Influenza A/Sydney/5/97 [H3N2] allantoic stock.

TABLE 25

Treatment Group Distribution Assignment

| Group | Number of Ferrets | Treatment |
|---|---|---|
| 1 | 5 | Placebo-Transmission |
| 2 | 5 | Placebo-Prophylaxis |
| 3 | 10 | QR435-Prophylaxis |
| 4 | 10 | QR435-Transmission |
| 5 | 10 | Tamiflu ™-Prophylaxis |
| 6 | 10 | Tamiflu ™-Transmission |

Groups 3 and 4 in the protocol are shown as group 3 above, groups 4 and 5 are shown as group 4 above, groups 7 and 8 are shown as group 5 above and groups 9 and 10 are shown as group 6 above. The groups were paired and subdivided into groups of 5 for animal welfare reasons only.

TABLE 26

Infection status of the donor animals

| Ferret ID # | Group | Nasal symptoms | Systemic symptoms | Seroconversion | Virus shedding |
|---|---|---|---|---|---|
| 037284841 | Placebo-Transmission | Y | Y | Y | N |
| 034537339 | Placebo-Prophylaxis | Y | Y | Y | N |
| 034543003 | QR435 Prophylaxis | Y | N | Y | N |
| 036534054 | QR435 Prophylaxis | Y | Y | Y | N |
| 034540555 | QR435 Transmission | Y | Y | No sample | Low |
| 036788799 | QR435 Transmission | Y | N | No sample | Low |
| 036803821 | Tamiflu ™ Prophylaxis | N | Y | Y | Low |
| XXXC | Tamiflu ™ Prophylaxis | Y | Y | Y | N |
| XXXD | Tamiflu ™ Transmission | Y | Y | Y | N |
| 036800314 | Tamiflu ™ Transmission | Y | Y | Y | Low |

Transmission Study

The object of the transmission study was to determine whether the test compound could prevent a donor ferret from transmitting influenza virus to non-infected recipient ferrets in the same pen. One ferret per group was inoculated with virus, and approximately 5 minutes after inoculation, the remaining uninoculated animals were administered either the test or the control compound. The volume of test compound or control was 0.14 ml per nostril for a total of 0.28 ml per dosing time. The inoculated animal was isolated for 24 hours then re-introduced to the appropriate group on day 1. The inoculated animal was treated twice daily with the test compound or appropriate control. The remaining ferrets were not treated throughout the duration of the experiment. On days 0 through 6 all ferrets were observed for clinical signs, weight loss and fever. Intranasal wash collection was performed on day 6, the volume of wash recovered measured and the weight of the nasal wash noted in the laboratory notebook. Viral titer of the recovered nasal washes was determined using MDCK cells.

Tables 27–31 show the results of the transmission experiment. Table 27 shows the percentage of animals with nasal symptoms of influenza.

TABLE 27

Percentage of animals with nasal symptoms of influenza (donor animals excluded)

| | Day | | | | | |
|---|---|---|---|---|---|---|
| GROUP | 1 | 2 | 3 | 4 | 5 | 6 |
| Placebo | 0% | 0% | 0% | 100% | 75% | 50% |
| Tamiflu ™ | 0% | 12.5% | 37.5 | 50% | 0% | 12.5% |
| QR435 | 0% | 0% | 0% | 0% | 25% | 37.5% |

Table 28 shows the percentage of animals with reduced physical activity.

TABLE 28

Percentage of animals with reduced physical activity (donor animals excluded)

| | Day | | | | | |
|---|---|---|---|---|---|---|
| GROUP | 1 | 2 | 3 | 4 | 5 | 6 |
| Placebo | 0% | 0% | 0% | 100% | 0% | 0% |
| Tamiflu ™ | 0% | 0% | 0% | 0% | 0% | 12.5% |
| QR435 | 0% | 12.5% | 0% | 0% | 12.5% | 0% |

The various criteria for influenza illness were considered and used to determine the percentage of animals showing symptoms. When nasal symptoms were considered (Table 27), by day 4, 100% (4/4) of the animals in the placebo group had symptoms of influenza, whereas, by contrast on day 4 only 50% (4/8) of animals had symptoms in the Tamiflu™ treated group. None of the animals in the QR435 treatment group had symptoms. By day 6 however 37.5% of the animals in the QR435 treatment group had nasal symptoms. It is unclear as to whether these were caused by influenza infection or irritation from the nasal spray.

When systemic signs of influenza such as reduced activity are considered, by day 4, all (4/4) animals in the placebo group had symptoms, however only a single animal (12.5%) showed signs of illness on any day post infection in the active treatment groups.

Table 29 shows laboratory confirmed influenza and seroconversion by the treatment group. Each animal was bled before challenge and on day 24, post infection so that influenza infection could be confirmed by serology. Seroconversion was defined as a four-fold rise in anti HAI antibodies against A/Sydney/5/97 (H3N2). In Table 29 it is shown that 100% of animals in both the placebo treatment group and the Tamiflu™ treatment group seroconverted. However, only 57% (4/7) of those animals tested seroconverted in the QR435 treatment group. Due to equipment failure one serum sample could not be tested.

TABLE 29

Laboratory confirmed influenza; Seroconversion by treatment group

| | # of animals seroconverted | Percentage of animals seroconverted |
|---|---|---|
| Placebo | 4/4 | 100 |
| QR435 | 4/7* | 57 |
| Tamiflu ™ | 8/8 | 100 |

*one animal was culled early and no sample taken

Table 30 shows the mean virus shedding from the nasal mucosa on day 6 post infection. Nasal washes were performed on day 6 post infection and the samples titrated on MDCK cells for influenza virus. Table 30 shows a substantial difference in the number of animals shedding virus between the two active treatment groups. Only a single animal in the QR435 treatment group shed virus compared to all animals in the Tamiflu™ treatment group. Unexpectedly, only a single animal in the placebo group (25%) shed virus.

TABLE 30

Laboratory confirmed influenza; Virus shedding
from the nasal mucosa on day 6 post infection

| GROUP | # of animals shedding virus on day 6 | Percentage of animals shedding virus on day 6 |
|---|---|---|
| Placebo | 1/4 | 25% |
| QR435 | 1/7* | 14 |
| Tamiflu ™ | 8/8 | 100 |

*one animal was culled early and no sample taken

The mean virus shedding by treatment group was calculated and the differences compared by ANOVA. The result was found to be statistically significant (p=0.02). T-tests were performed using the Bonferroni correction for multiple testing and the Tamiflu™ treated group was found to shed significantly more virus than both the placebo treatment group (p=0.021) and the QR435 treatment group (p=0.04).

Table 31 is the mean maximum health score by treatment group. The mean and Standard Deviation of the maximum health score was calculated as described above in the prophylaxis study results. The results were significant (p=0.02). Individual groups were compared as described above and both treatment groups have significantly lower maximum health scores than the placebo group (QR435 p=0.006 and Tamiflu™ p=0.003).

TABLE 31

Mean Maximum Health Score by Treatment Group.

| Group | Mean | N | Std. Deviation |
|---|---|---|---|
| Placebo | 1.0000 | 4 | .00000 |
| QR435 | .8750 | 8 | .35355 |
| Tamiflu ™ | .7500 | 8 | .70711 |
| Total | 1.0500 | 20 | .68633 |

An AUC-like measure comprising the sum of health scores post infection was calculated for each animal; treatment group's means and Standard Deviations were calculated and compared ANVOA.

Table 32 shows the results and the difference between treatment groups was highly significant (p=0.002). Individual groups were compared using t-tests and the Bonferroni correction for multiple testing, both treatment groups had significantly lower total health scores than the placebo group (QR435 p=0.06 and Tamiflu™ p=0.03).

TABLE 32

Mean Total Health Score by Treatment Group

| Group | Mean | N | Std. Deviation |
|---|---|---|---|
| Placebo | 4.2000 | 4 | .95743 |
| QR435 | .3750 | 8 | .64087 |
| Tamiflu ™ | .5000 | 8 | .83452 |
| Total | 1.5000 | 20 | 1.53125 |

The mean maximum weight change post infection was similarly calculated and compared by ANOVA. The results were not significant (p=0.90). Both treatment groups had significantly less weight loss than the placebo group (QR435 p=0.055 and Tamiflu™ p=0.019). The AUC like measure comparing the sum of the weight changes post infection was also calculated for each animal and compared by ANOVA. The difference between treatment groups was not significant (p=0.64).

Prophylaxis Study

The object of the prophylaxis study was to determine whether treatment of uninfected recipient ferrets with the test compound could prevent viral infection from an infected donor. One ferret per group was inoculated with virus, and approximately 5 minutes after inoculation, the remaining uninoculated animals were administered either the test or the control compound. The inoculated animal was isolated for 24 hours then re-introduced to the appropriate group on day 1. The inoculated animal was not treated with the test compound or appropriate control. The remaining ferrets were treated with the test compound or appropriate control twice daily. The volume of test compound or control was 0.14 ml per nostril for a total of 0.28 ml per dosing time. On days 0 through 6 all ferrets were observed for clinical signs, weight loss and fever. Intranasal wash collection was performed on day 6, the volume of wash recovered measured and the weight of the nasal wash noted in the laboratory notebook. Viral titers of the recovered nasal washes were determined using MDCK cells. A bleed at 24 days was taken for control assays.

Each donor animal was successfully infected. Due to the parameters of the studies it was important to demonstrate that each donor animal was successfully infected, that each donor animal demonstrated clinical signs of infection and seroconversion. However, viral shedding was not detected in the nasal washings. It is not surprising that there was little or no viral shedding in the donor animals as viral shedding often ceases prior to day 6, the day the washing were taken.

Tables 33–38 show the results from the prophylaxis experiment. Table 33 shows the percentage of animals that had nasal symptoms of influenza. Table 34 shows the percentage animals that had reduced physical activity during the testing period.

TABLE 33

Percentage of animals with nasal symptoms of influenza
(donor animals excluded) by treatment group

| | Day | | | | | |
|---|---|---|---|---|---|---|
| GROUP | 1 | 2 | 3 | 4 | 5 | 6 |
| Placebo | 0 | 0 | 0 | 0 | 75% | 75% |
| Tamiflu ™ | 0 | 0 | 25% | 0 | 0% | 12.5 |
| QR435 | 0 | 0 | 0 | 0 | 25% | 25% |

TABLE 34

Percentage of animals with reduced physical
activity (donor animals excluded)

| | Day | | | | | |
|---|---|---|---|---|---|---|
| GROUP | 1 | 2 | 3 | 4 | 5 | 6 |
| Placebo | 0 | 0 | 100% | 100% | 0 | 0 |
| Tamiflu ™ | 0 | 0 | 0 | 0 | 0 | 0 |
| QR435 | 0 | 0 | 0 | 0 | 0 | 0 |

Prophylaxis Study Results

In the prophylaxis study, 75% of the placebo group (¾) had nasal symptoms of influenza infection by day 5, whereas 25% of the Tamiflu™ group had nasal symptoms by day 3 and 25% of the QR435 group had nasal symptoms by day 5. When the percentage of animals showing reduced physical activity is considered the results are more dramatic in that 100% of the placebo group showed reduced physical activity and none of the animals from either of the Tamiflu™ or the QR435 group showed any signs of reduced activity. Table 35 shows the mean maximum health score by treatment group. The mean and standard deviation of the maximum health score for each animal was calculated by treatment group then compared by ANOVA. The results approached significance (p=0.087).

TABLE 35

Mean Maximum Health Score by Treatment Group

| Group | Mean | N | Std. Deviation |
| --- | --- | --- | --- |
| Placebo | 1.0000 | 4 | .00000 |
| QR435 | .3750 | 8 | .51755 |
| Tamiflu ™ | .3750 | 8 | .51755 |
| Total | .5000 | 20 | .51299 |

An AUC-like measure comprising the sum of health scores post infection was calculated for each animal; treatment group's means and Standard Deviations were calculated and compared ANVOA. Table 35 shows the results and the difference between treatment groups was highly significant (p<0.0005). Individual groups were compared using t-tests and the Bonferroni correction for multiple testing, both treatment groups had highly significantly lower total health scores than the placebo group.

TABLE 36

Mean Total Health Score by Treatment Group

| Group | Mean | N | Std. Deviation |
| --- | --- | --- | --- |
| Placebo | 3.5000 | 4 | 1.00000 |
| QR435 | .3750 | 8 | .51755 |
| Tamiflu ™ | .5000 | 8 | .75593 |
| Total | 1.5000 | 20 | 1.43178 |

Each animal was bled before challenge and on day 24, post infection, so that influenza infection could be confirmed by serology. Seroconversion is a four-fold increase in HAI antibodies against the inoculation strain.

TABLE 37

Laboratory confirmed influenza; Seroconversion by treatment group

|  | # of animals seroconverted | Percentage of animals seroconverted |
| --- | --- | --- |
| Placebo | 2/2* | 100% |
| QR435 | 0/8 | 0% |
| Tamiflu ™ | 8/8 | 100% |

Table 38 shows laboratory confirmed influenza and the percentage of animals virus shedding on day 6 post infection of the treatment group. Nasal washes were performed on day 6 post infection and the samples titrated on MDCK cells for influenza virus. Table 38 shows that there is a substantial difference in the number of animals shedding virus between the two active treatment groups, i.e., for the QR435 treated group none of the animals shed virus compared to 75% in the placebo treated group and 87.5% in the Tamiflu™ treated group.

TABLE 38

Laboratory confirmed influenza; Virus shedding on day 6 post infection by treatment group

|  | # of animals shedding virus on day 6 | Percentage of animals shedding virus on day 6 |
| --- | --- | --- |
| Placebo | 3/4 | 75% |
| QR435 | 0/8 | 0% |
| Tamiflu ™ | 7/8 | 87.5% |

The mean virus shedding by treatment group was calculated and the differences compared by ANOVA. The result was found to be statistically significant (p=0.001). T-tests were performed using the Bonferroni correction for multiple testing and the QR435 treated group was found to shed significantly less virus than both the placebo treatment group (p=0.004) and the Tamiflu™ treatment group (p=0.002).

The mean and standard deviation of the maximum weight change for each animal was calculated by treatment group and then compared by ANOVA. The results were significant (p=0.018). Individual groups were compared using t-tests and the Bonferroni correction for multiple comparisons. Both treatment groups had significantly less (or very close to) weight loss than the placebo treatment group (QR435 p=0.055 and Tamiflu™ p=0.019).

An AUC-like measure comprising the sum of the weight changes post infection was calculated for each animal; treatment group means and Standard Deviations were calculated and compared by ANOVA. The difference between treatment groups was not significant (p=0.461).

The mean maximum weight change post infection was similarly calculated and compared by ANOVA. The results were significant (p=0.018). Both treatment groups had significantly less weight loss than the placebo group (QR435 p=0.055 and Tamiflu™ p=0.019). The AUC like measure comparing the sum of the weight changes post infection was also calculated for each animal and compared by ANOVA. The difference between treatment groups was not significant (p=0.461).

Conclusion

The positive treatment group that was treated with Tamiflu™ (oseltamivir phosphate, administered at 5 mg/kg twice daily) was generally protected from the symptoms of influenza in both the transmission and prophylaxis experiments. On the other hand, these animals were infected as shown by both viral shedding and the seroconversion of the recipient animals. In contrast, the test compound QR-435 was 100% effective in preventing infection and partially effective in preventing transmission. Thus, the important benefit of the compound is its ability to prevent infection, particularly the suppression of the shedding of viral particles which would reduce the spread of disease.

EXAMPLE 10

In Vitro Comparison of the Virucidal and Virustatic Activity Against the SARS Virus Two compositions QR439 and QR439(a) were tested in vitro for virucidal and virustatic activity against the SARS virus. QR439 was formulated as follows:

| (1) | Aquaresin ® ginger | 0.6849% by weight |
| (2) | Oleoresin turmeric | 0.6466% by weight |
| (3) | Green Tea PE | 0.4619% by weight |
| (4) | Glycerin | 49.1039% by weight |
| (5) | Deionized water | 49.1039% by weight |

Qr439(a) was formulated as follows:

| (1) | Aquaresin ® ginger | 0.6840% by weight |
| (2) | Oleoresin turmeric | 0.6466% by weight |
| (3) | Green Tea PE | 0.4619% by weight |
| (4) | Horseradish oil | 0.063192% by weight |
| (5) | Glycerin | 49.0723% by weight |
| (6) | Deionized water | 49.0723% by weight |

In the test, the positive control compounds were: 1% Triton-X 100 (in artificial saliva [0.1% $NaHCO_3$, 18% $KH_2PO_4$, 0.1% gastric mucin, pH adjusted to 6.0–6.5]) for the virucidal assay and Ribavirin (200 µ/ml) in 1% DMSO (in PBS) for the virustatic assay.

The negative control compound was Artificial Saliva (0.1% $NaHCO_3$, 18% $KH_2PO_4$, 0.1% gastric mucin, pH adjusted to 6.0–6.5) for the virucidal assay only. Urbani SARS virus was used at a stock titer of $10^5$ $TCID_{50}$/ml. The test compounds, QR439 and QR439(a) were diluted in Sterets Normasol (Seton Prebbles Ltd) to produce the following dilutions for the virucidal assay: 1/10, 1/20, 1/40, 1/80, 1/160, 1/320, and 1/640.

Virucidal Assay Method

Residual virus titers were titrated on C1008 (a clone of Vero 76) cells for viral growth in 96-well plates. The results were analyzed for CPE (cytopathic effect) and the virus titer determined using the Karber method.

The following steps were conducted in performing the virucidal assay. 360 µl of the test compound was mixed with 40 µl virus. The mixture was agitated and then incubated for 30 seconds, 1, 2, 4 or 8 minutes. The reaction was terminated at a specific time by adding 3.6 ml of infection media (DMEM, 2 mM L-glutamine, HEPES, penicillin-streptomycin). Termination is caused by the dilution effect of the addition of the infection media because both the virus and test compounds are diluted ten-fold in this step. Residual virus infectivity was titrated on C1008 cells at 10 fold dilutions across the 96-well plate. The C1008 cells were incubated for 7–10 days at 37° C. The results were scored for CPE and virus titer calculated. The cells were examined for CPE on Days 3, 4, and 5 post-infection.

Cytotoxicity Assay Method

A cytotoxicity assay on C1008 cells was carried out on all three compounds to determine which dilutions to use for the virustatic assay. 200 µl of each test compound, and control compound, was added to the first wells (in duplicate) of a 96-well plate and then titrated across the plate following a 2-fold dilution series. The plate was incubated at 35° C., 5% $CO_2$. The cells were observed for CPE after 3 days incubation.

Virustatic Assay Method

The dilutions that were used for the virustatic assay are as follows: QR439 and QR439(a) at the following dilutions: 1/200, 1/300, 1/400, 1/500, 1/600. Infection media (DMEM, 2 mM L-glutamine, HEPES, penicillin-streptomycin) was used to dilute each test compound, as appropriate. 100 µl of each diluted test compound, and the positive control, were added to wells of C1008 cells (in duplicate) and then incubated for 30 minutes at 35° C., 5% $CO_2$. After the incubation period, 10 µl of Urbani SARS virus (at a stock titer of $10^5$ $TCID_{50}$/ml) was added to each well of the test compounds and positive control. The plate was incubated at 35° C., 5% $CO_2$ for 3–5 days before observing the cells for CPE. A crystal violet assay, which measured the OD (optical density) of the cells, was performed on the plate after the CPE was recorded. The OD values were used to determine the $TC_{50}$ and $EC_{50}$ of the test compounds.

Results

The results of the cytotoxicity assay performed on the test compounds are shown in Table 39 shown below. Each undiluted compound was added in duplicate to wells in the first column of the plate and diluted across the plate in a 2-fold dilution series. The concentration within the range of the 1/8 and 1/16 dilutions is equivalent to the concentration of the test compounds that were added to the plates in the virucidal assay. This is because the compounds were diluted 1/10 when the termination media was added.

TABLE 39

| Test Compound | Cytotoxicity Assay 2-Fold Dilution Series | | | | | | | | | |
|---|---|---|---|---|---|---|---|---|---|---|
| | UD | 1/2 | 1/4 | 1/8 | 1/16 | 1/32 | 1/64 | 1/128 | 1/256 | 1/512 |
| QR439 | + | + | + | + | + | + | + | + | – | – |
| QR439(a) | + | + | + | + | + | + | + | + | – | – |
| Cells Only | – | – | – | – | – | – | – | – | – | – |

+ both wells exhibited toxicity
– both wells exhibit non-toxicity
+/1 one well exhibits toxicity, the other well exhibits non-toxicity Table 39 demonstrates that both test compounds are toxic to the cells at the 1/8 dilution (which is equivalent to the dilution used in the virucidal assay for the undiluted compounds). In the virucidal and virustatic assays, a dilution of greater than 1/128 was needed to eliminate toxicity.

The CPE observations (Table 40) show that there was no virustatic activity detected for any of the three compounds tested.

TABLE 40

CPE Observations

|  |  | QR439 | QR439(a) | Ribovirin | Cells only | Virus Control |
|---|---|---|---|---|---|---|
| Dilutions* of Test Compounds | A | + | + | T | − | + |
|  | B | + | + | T | − | + |
|  | C | + | + | T | − | + |
|  | D | + | + | T | − | + |
|  | E | + | + | T | − | + |
|  | F | ND | ND | T | − | + |
| 10-Fold Dilutions |  | Undiluted | 10 | $10^3$ | $10^4$ | $10^5$ |
| Undiluted Virus |  | + | + | +/− | − | − |

+ Virus infection in both wells
− No viral infections in both wells
+/− Viral infection in one well no infection in the other well
T Toxicity in both wells
ND Virustatic assay not done at a sixth serial dilution
*Dilutions used for QR439 and QR439(a) are A = 1/200, B = 1/300, C = 1/400, D = 1/500, E = 1/600

The results of the virucidal assay performed on the test compounds QR439 and QR439(a) are represented in Table 41 and Table 42 respectively. The Tables indicate the reduction in viral titer after 1/10 dilution of the test compounds, which is equivalent to a 1/10 dilution of the undiluted virus.

TABLE 41

Log reduction in Viral Titer after contact with Test Compound QR439
Log Reduction in Viral Titer ($-\log_{10}TCID_{50}$/ml)

| Initial Dilution | Test Compound Contact Times (minutes) | | | | | Virus Control Titer[a] |
|---|---|---|---|---|---|---|
|  | 0.5 | 1 | 2 | 4 | 8 |  |
| Undiluted | T | T | T | T | T | 2.5 |
| 1/10 | ≧1.0 | ≧1.0 | ≧1.0 | ≧1.0 | ≧1.0 | 2.5 |
| 1/20 | ≧1.0 | ≧1.0 | ≧1.0 | ≧1.0 | ≧1.0 | 2.5 |
| 1/40 | 2.5* | 2.5* | 2.5* | 2.5* | 2.5* | 3.0 |
| 1/80 | 2.0* | 2.0* | 2.0* | 2.0* | 2.0* | 2.5 |
| 1/160 | 2.5* | 2.5* | 2.0 | 2.5* | 2.5* | 3.0 |
| 1/320 | 0.0 | 1.5 | 1.0 | 1.5 | 2.5* | 3.0 |
| 1/640 | 0.0 | 0.5 | 1.5 | 0.5 | 1.0 | 3.0 |

[a]$-\log_{10}TCID_{50}$/ml
*No virus recovery. However using the Karber Calculation method (taking into account the initial 1/10 dilution) a titer of 0.5 $TCID_{50}$/ml is obtained

TABLE 42

Log reduction in Viral Titer after contact with Test Compound QR439(a)
Log Reduction in Viral Titer ($-\log_{10}TCID_{50}$/ml)

| Initial Dilution | Test Compound Contact Times (minutes) | | | | | Virus Control Titer[a] |
|---|---|---|---|---|---|---|
|  | 0.5 | 1 | 2 | 4 | 8 |  |
| Undiluted | T | T | T | T | T | 2.5 |
| 1/10 | ≧1.0 | ≧1.0 | ≧1.0 | ≧1.0 | ≧1.0 | 2.5 |
| 1/20 | 2.0* | 2.0* | 2.0* | ≧1.0 | ≧1.0 | 2.5 |
| 1/40 | 2.0* | 2.0* | 2.0* | 2.0* | 2.0* | 3.0 |
| 1/80 | 2.0 | 2.0 | 2.5* | 2.5* | 2.5* | 2.5 |
| 1/160 | 2.5 | 3.0* | 3.0* | 3.0* | 3.0* | 3.0 |
| 1/320 | 0.0 | 0.5 | 0.0 | 0.5 | 1.0* | 1.5 |
| 1/1/640 | 0.5 | 0.5 | 1.5 | 0.5 | 0.0 | 2.5 |

[a]$-\log_{10}TCID_{50}$/ml
*No virus recovery. However using the Karber Calculation method (taking into account the initial 1/10 dilution) a titer of 0.5 $TCID_{50}$/ml is obtained The results show that for QR439, there is a significant reduction in virucidal activity from the 1/40 to 1/640 dilutions at all contact time points, with the exception of 1/320 (30 seconds) and 1/640 (30 seconds, 1 minute, and 4 minutes). The results show that for QR439(a) there is a significant reduction in virucidal activity from the 1/20 to 1/60 dilutions at all contact time points with the exception of 1/20 (4 and 8 minutes).

EXAMPLE 11

Efficacy of Antimicrobial Nasal Spray on H3N2 Influenza Infection

Forty ferrets were infected with influenza A/Sydney/5/97 [H3N2] and treated with QR435, as employed in Example 9 above, or control compounds daily for 4 days. Clinical signs were measured alongside weights, rectal temperatures, cell counts, and virus shedding. The virus inoculum A/Sydney/5/97 was virulent and signs of illness were observed, with the placebo treated (PBS) ferrets exhibiting distinct symptoms of influenza A infection. The positive control (Tamiflu™) was effective at reducing weight loss, fever, and clinical symptoms. No reduction of illness was noted in the QR435 administered groups.

The test substance was a nasal spray containing 1.8% active compound with the formula as noted in example 9 above. The positive control substance was Tamiflu™ (Oseltamivir phosphate) administered at 5 mg/kg twice daily. Phosphate buffered saline (as a nasal spray) was also be used as a control and administered intranasal four times a day.

The challenge virus was A/Sydney/5/97 [H3N2] was from the Retroscreen virus repository. The ferrets were successfully infected with influenza and exhibited the classical signs of the associated disease in the PBS treatments group (negative control). The Tamiflu™ treatment group (positive control) showed reduction in the severity of the disease with statistically significant (or almost significant) reductions in, virus shedding, weight loss, and illness scores.

Neither of the two test compound treatment groups (QR435 twice daily and QR435 four times daily) demonstrated reduced illness for treatment purposes. However, as noted in example 9 above, QR435 has proven effective for anti-transmissivity and prophylactic uses.

EXAMPLE 12

In an effort to reduce the irritant properties of the nasal spray, yet retain the anti-transmissivity properties previously demonstrated, the efficacy of varying horseradish concentrations was tested in the ferret model. The QR-435 full horseradish ALS sialorrhea spray formulation was as follows:

QR-435 Formulation

| Oleoresin Turmeric | 0.0308 weight percent |
| Aquaresin ® Ginger | 0.0326 weight percent |
| Horseradish Oil #58 | 0.00300 weight percent |
| Green Tea PE 030725 | 0.0220 weight percent |
| Glycerin | 2.3368 weight percent |
| Deionized Water | 97.5749 weight percent |

In the 50% horseradish test formulation, the horseradish oil was reduced to 0.0015% by weight and the glycerin and deionized water increased by 0.000075% by weight. Similarly, in the 25% horseradish study, the horseradish oil was reduced to 0.000075 and the glycerin and deionized water increased by 0.001125% by weight.

Table 43 shows the distribution of the various ferret groups and the pen treatment protocol. Each group was subdivided into two pens strictly for logistical reasons. Each group consisted of four recipient animals and one donor animal.

TABLE 43

Group Distribution

| Group | Number of Ferrets | Treatment |
|---|---|---|
| 1a | 5 | Placebo (PBS) QDS |
| 1b | 5 | Placebo (PBS) QDS |
| 2a | 5 | QR435 100% Horseradish QDS |
| 2b | 5 | QR435 100% Horseradish QDS |
| 3a | 5 | QR435 50% Horseradish QDS |
| 3b | 5 | QR435 50% Horseradish QDS |
| 4a | 5 | QR435 25% Horseradish QDS |
| 4b | 5 | QR435 25% Horseradish QDS |
| 5a | 5 | Tamiflu ™ 5 mg/kg BDS |
| 5b | 5 | Tamiflu ™ 5 mg/kg BDS |

QDS = 4 times dosing per day intranasally
BDS = 2 times dosing per day orally

The animals were electronically tagged using programmable injectable transponders for animal identification and body temperature monitoring. Blood samples were taken from superficial veins and the terminal bleed was taken by cardiac puncture.

Donor ferrets where infected intranasally as follows: one animal from the group of five was removed and infected with 0.5 ml of virus (0.25 ml per nostril) while the animal was under anesthetic. The donor animals were not treated with the test material. Recipient ferrets were treated according to the treatment group assignment as outlined in Table 43 and study schedule in Table 44. Nasal wash collection was performed and the volume of nasal wash recovered was measured and weighed to determine the volume of nasal wash recovery.

The HI assay was performed upon the sample against homologous virus to determine the seronegativity of the ferrets as well as determining the extent of seroconversion, if any, following infection. Health scores, body weight and temperature were recorded. Total cell counts on the nasal washing samples were determined using trypan blue in order to evaluate the inflammatory cell response recovered from the nasal epithelium. Virus shedding from the nasal washes were performed using MDCK cells.

TABLE 44

Study Schedule

| Day | 0 | 1 | 2 | 3 | 4 | 5 | 6 | 16 |
|---|---|---|---|---|---|---|---|---|
| Electronic Tagging | X | | | | | | | |
| Anesthesia | X | | | | | | | X |
| Temperature | X | X | X | X | X | X | X | |
| Body Weight | X | X | X | X | X | X | X | |
| Health score | X | X | X | X | X | X | X | |
| Infection of Donor | X | | | | | | | |
| Isolation of Donor | X | | | | | | | |
| Integration of Donor | | X | | | | | | |
| Nasal wash | | | | | | | X | |
| Serum for HAI | X | | | | | | | X |
| Test Article Dosing Recipient | X | X | X | X | X | X | X | |

Table 45 shows the clinical signs of the donor animals after exposure to the influenza virus. As can be seen from the table, each donor animal was successfully infected with influenza virus.

TABLE 45

Donor Clinical Signs

| Pen* | % Weight Loss (Peak to Trough) | Fever >1SD, >2SD, or >3SD | Sero-conversion |
|---|---|---|---|
| 1a | 0.80 | >3SD | Y |
| 1b | 2.31 | >3SD | Y |
| 2a | 2.88 | >3SD | Y |
| 2b | 0.91 | >3SD | Y |
| 3a | 1.90 | >2SD | Y |
| 3b | 1.43 | >2SD | Y |
| 4a | 2.76 | >2SD | Y |
| 4b | 1.15 | >3SD | Y |
| 5a | 2.49 | >1SD | Y |
| 5b | 0.93 | >2SD | Y |

*See Table 43 for Treatment Protocol

Influenza related illness in the recipient ferrets was determined using the following parameters: weight loss, fever, virus shedding, seroconversion, clinical nasal and activity signs, nasal cell counts. The control groups (PBS treated groups 1a and 1b) exhibited typical signs of influenza illness that included weight loss, fever, seroconversion, and the presence of some clinical signs of illness (including activity and nasal signs). The Tamiflu™ treatment groups did not show any overt clinical signs and did not seroconvert, therefore the Tamiflu™ treatment was confirmed as being effective at reducing influenza illness. Comparison of the percentage weight loss between groups suggests that there is a difference in illness. The weight loss was calculated by finding the peak weight of each ferret followed by identifying the subsequent trough. The difference in weight between peak and trough was calculated as a percentage of the baseline weight as taken on day 0. When the groups were compared for weight loss by treatment, several treatments exhibited significant reductions in illness. The results from Table 46 indicate that PBS treated group was significantly different from all other treatments. (PBS vs. 100% horseradish p=0.008; PBS vs. 50% horseradish p=0.022; PBS vs. 25% horseradish p=0.005; PBS vs. Tamiflu™ p=0.003).

Thus, the test compound was as effective as the positive control (Tamiflu™) at preventing weight loss in animals infected with influenza via the natural transmission route, from another ferret.

TABLE 46A

Results Comparison
Dependent Variable: Weight Change separated into pens

| Group Number | Mean | Std. Error | 95% Confidence Interval | |
|---|---|---|---|---|
| | | | Lower Bound | Upper Bound |
| PBS | −2.860 | .405 | −3.686 | −2.034 |
| 100% horseradish | −1.231 | .405 | −2.057 | −.405 |
| 50% horseradish | −1.478 | .405 | −2.304 | −.651 |
| 25% horseradish | −1.141 | .405 | −1.967 | −.315 |
| Tamiflu ™ | −.980 | .405 | −1.806 | −.154 |

TABLE 46B

Pairwise Comparison
Dependent Variable: Weight Change separated into pens

| (I) Group Number | (J) Group Number | Mean Difference (I−J) | Std. Error | Sig.[a] | 95% Confidence Interval Lower Bound | 95% Confidence Interval Upper Bound |
|---|---|---|---|---|---|---|
| PBS | 100% Horseradish | −1.629 | .572 | .008 | −2.797 | −.460 |
|  | 50% horseradish | −1.382 | .572 | .022 | −2.551 | −.214 |
|  | 25% horseradish | −1.719 | .572 | .005 | −2.887 | −.550 |
|  | Tamiflu ™ | −1.880 | .572 | .003 | −3.048 | −.712 |
| 100% horseradish | PBS | 1.629 | .572 | .008 | .460 | 2.797 |
|  | 50% horseradish | 2.46 | .572 | .670 | −.922 | 1.415 |
|  | 25% horseradish | −9.000E−02 | .572 | .876 | −1.258 | 1.078 |
|  | Tamiflu ™ | −.251 | .572 | .664 | −1.420 | .917 |
| 50% horseradish | PBS | 1.382 | .572 | .022 | .214 | 2.551 |
|  | 100% Horseradish | −.246 | .572 | .670 | −1.415 | .922 |
|  | 25% horseradish | −.336 | .572 | .561 | −1.505 | .832 |
|  | Tamiflu ™ | −.497 | .572 | .391 | −1.666 | .671 |
| 25% horseradish | PBS | 1.719 | .572 | .005 | .550 | 2.887 |
|  | 100% Horseradish | −9.000E−02 | .572 | .876 | −1.078 | 1.258 |
|  | 50% horseradish | .336 | .572 | .561 | −1.666 | 1.505 |
|  | Tamiflu ™ | −.161 | .572 | .780 | −1.330 | 1.007 |
| Tamiflu | PBS | −1.880 | .572 | .003 | .712 | 3.048 |
|  | 100% Horseradish | .251 | .572 | .664 | −.917 | 1.420 |
|  | 50% horseradish | .497 | .572 | .391 | −.671 | 1.666 |
|  | 25% horseradish | .161 | .572 | .780 | −1.007 | 1.330 |

[a]Adjustments for multiple comparisons: least significant difference (equivalent to no adjustments)

Individual ferrets that showed temperature rises greater than 3 SD (Standard Deviations) from the previous temperature measurement were deemed to have a strong febrile illness. For each group the SD was calculated from each group's mean temperature on Day 1. Due to the use of anesthesia on Day 0, and possible subsequent modifications of ferret temperature, Day 1 temperatures were deemed more appropriate to be used to generate the baseline mean and SD. Table 47 is a summary of fever as defined as a 3 SD rise from the previous temperature measurement.

TABLE 47

Results Comparison

| Pen Number* | No. of Ferrets per pen with Fever (>3SD rise) | Group Number | No. of ferrets per group with Fever (>3SD rise) |
|---|---|---|---|
| 1a | 2 | 1 | 4 |
| 1b | 2 |  |  |
| 2a | 1 | 2 | 1 |
| 2b | 0 |  |  |
| 3a | 0 | 3 | 1 |
| 3b | 1 |  |  |
| 4a | 3 | 4 | 5 |
| 4b | 2 |  |  |
| 5a | 0 | 5 | 1 |
| 5b | 1 |  |  |

*See Table 43 for Pen Treatment Protocol

TABLE 48

Mild Febrile Illness

| Pen Number* | No. of Ferrets per pen with Fever (>2SD rise) | Group Number | No. of ferrets per group with Fever (>2SD rise) |
|---|---|---|---|
| 1a | 3 | 1 | 7 |
| 1b | 4 |  |  |
| 2a | 2 | 2 | 4 |
| 2b | 2 |  |  |
| 3a | 1 | 3 | 2 |
| 3b | 1 |  |  |
| 4a | 3 | 4 | 5 |
| 4b | 2 |  |  |
| 5a | 2 | 5 | 4 |
| 5b | 2 |  |  |

*See Table 43 for Pen Treatment Protocol

Using $X^2$ analysis of the fever as defined by a 3SD rise from the previous temperature measurement the following was determined:

PBS treatment vs. 50% horseradish p=0.106 (Table 49)
PBS vs. 10% horseradish p=0.106 (Table 50)
PBS vs. Tamiflu™ p=0.106 (Table 51)

Table 48 summarizes the number of ferrets with a clear temperature rise of more than 2SD from the previous temperature measurement, which were deemed to have a mild febrile illness.

TABLE 49

$X^2$ analysis of the number of ferrets with fever between PBS and 50% horseradish treatment (>3SD rise in temperature from baseline)

|  |  |  | Group Number | | |
|---|---|---|---|---|---|
|  |  |  | PBS | 100% horseradish | Total |
| Fever => 3SD rise from baseline | No | Count | 4 | 7 | 11 |
|  |  | Expected count | 5.5 | 5.5 | 11.0 |
|  |  | % within Group No. | 50.0% | 87.5% | 68.8% |
|  | yes | Count | 4 | 1 | 5 |
|  |  | Expected count | 2.5 | 2.5 | 5.0 |
|  |  | % within Group No. | 50.0% | 12.5% | 31.3% |
| Total |  | Count | 8 | 8 | 16 |
|  |  | Expected count | 8.0 | 8.0 | 16.0 |
|  |  | % within Group No. | 100% | 100% | 100% |

Chi-Squared Tests

|  | Value | df | Asymp. Sig. (2-sided) | Exact Sig. (2-sided) | Exact Sig. (1-sided) |
|---|---|---|---|---|---|
| Pearson Chi-Square | 2.618[b] | 1 | .106 |  |  |
| Continuity Correction[a] | 1.164 | 1 | .281 |  |  |
| Likelihood Ration | 2.756 | 1 | .097 |  |  |
| Fisher's Exact Test |  |  |  | .282 | .141 |
| Linear-by-Linear Association | 2.455 | 1 | .117 |  |  |
| N of Valid Cases | 16 |  |  |  |  |

[a]Computed only for 2 × 2 table
[b]2 cells (50.0%) have expected count less than 5. The maximum expected count is 2.50.

TABLE 50

$X^2$ analysis of the number of ferrets with fever between PBS and 100% horseradish treatment (>3SD rise in temperature from baseline)

|  |  |  | Group Number | | |
|---|---|---|---|---|---|
|  |  |  | PBS | 50% horseradish | Total |
| Fever => 3SD rise from baseline | No | Count | 4 | 7 | 11 |
|  |  | Expected count | 5.5 | 5.5 | 11.0 |
|  |  | % within Group No. | 50.0% | 87.5% | 68.8% |
|  | yes | Count | 4 | 1 | 5 |
|  |  | Expected count | 2.5 | 2.5 | 5.0 |
|  |  | % within Group No. | 50.0% | 12.5% | 31.3% |
| Total |  | Count | 8 | 8 | 16 |
|  |  | Expected count | 8.0 | 8.0 | 16.0 |
|  |  | % within Group No. | 100% | 100% | 100% |

Chi-Squared Tests

|  | Value | df | Asymp. Sig. (2-sided) | Exact Sig. (2-sided) | Exact Sig. (1-sided) |
|---|---|---|---|---|---|
| Pearson Chi-Square | 2.618[b] | 1 | .106 |  |  |
| Continuity Correction[a] | 1.164 | 1 | .281 |  |  |
| Likelihood Ration | 2.756 | 1 | .097 |  |  |
| Fisher's Exact Test |  |  |  | .282 | .141 |
| Linear-by-Linear Association | 2.455 | 1 | .117 |  |  |
| N of Valid Cases | 16 |  |  |  |  |

[a]Computed only for 2 × 2 table
[b]2 cells (50.0%) have expected count less than 5. The maximum expected count is 2.50.

TABLE 51

$X^2$ analysis of the number of ferrets with fever between PBS and Tamiflu ™ treatment (>3SD rise in temperature from baseline)

|  |  |  | Group Number | | |
|---|---|---|---|---|---|
|  |  |  | PBS | 50% horseradish | Total |
| Fever => 3SD rise from baseline | No | Count | 4 | 7 | 11 |
|  |  | Expected count | 5.5 | 5.5 | 11.0 |
|  |  | % within Group No. | 50.0% | 87.5% | 68.8% |
|  | yes | Count | 4 | 1 | 5 |
|  |  | Expected count | 2.5 | 2.5 | 5.0 |
|  |  | % within Group No. | 50.0% | 12.5% | 31.3% |
| Total |  | Count | 8 | 8 | 16 |
|  |  | Expected count | 8.0 | 8.0 | 16.0 |
|  |  | % within Group No. | 100% | 100% | 100% |

Chi-Squared Tests

|  | Value | df | Asymp. Sig. (2-sided) | Exact Sig. (2-sided) | Exact Sig. (1-sided) |
|---|---|---|---|---|---|
| Pearson Chi-Square | 2.618[b] | 1 | .106 |  |  |
| Continuity Correction[a] | 1.164 | 1 | .281 |  |  |
| Likelihood Ration | 2.756 | 1 | .097 |  |  |
| Fisher's Exact Test |  |  |  | .282 | .141 |
| Linear-by-Linear Association | 2.455 | 1 | .117 |  |  |
| N of Valid Cases | 16 |  |  |  |  |

[a]Computed only for 2 × 2 table
[b]2 cells (50.0%) have expected count less than 5. The maximum expected count is 2.50.

Using $X^2$ analysis of the fever as defined by a 2SD rise from the previous temperature measurement the following was determined:

PBS treatment vs. 50% horseradish p=0.012 (Table 52)
PBS vs. 10% horseradish p=0.106 (Table 53)
PBS vs. Tamiflu™ p=0.106 (Table 54)

TABLE 52

$X^2$ analysis of the number of ferrets with fever between PBS and 50% horseradish treatment (>2SD rise in temperature from baseline)

|  |  |  | Group Number | | |
|---|---|---|---|---|---|
|  |  |  | PBS | 50% horseradish | Total |
| Fever => 2SD rise from baseline | No | Count | 1 | 6 | 7 |
|  |  | Expected count | 3.5 | 3.5 | 7.0 |
|  |  | % within Group No. | 12.5% | 75% | 68.8% |

TABLE 52-continued $X^2$ analysis of the number of ferrets with fever between PBS and 50% horseradish treatment (>2SD rise in temperature from baseline)

|  |  |  |  |  |
|---|---|---|---|---|
| | yes Count | 7 | 2 | 9 |
| | Expected count | 4.5 | 4.5 | 9.0 |
| | % within Group No. | 87.5% | 25% | 56.3% |
| Total | Count | 8 | 8 | 16 |
| | Expected count | 8.0 | 8.0 | 16.0 |
| | % within Group No. | 100% | 100% | 100% |

Chi-Squared Tests

| | Value | df | Asymp. Sig. (2-sided) | Exact Sig. (2-sided) | Exact Sig. (1-sided) |
|---|---|---|---|---|---|
| Pearson Chi-Square | 6.349[b] | 1 | .012 | | |
| Continuity Correction[a] | 4.063 | 1 | .044 | | |
| Likelihood Ration | 26.904 | 1 | .009 | | |
| Fisher's Exact Test | | | | .041 | .020 |
| Linear-by-Linear Association | 5.952 | 1 | .015 | | |
| N of Valid Cases | 16 | | | | |

[a]Computed only for 2 × 2 table
[b]4 cells (100.0%) have expected count less than 5. The maximum expected count is 3.50.

TABLE 53

$X^2$ analysis of the number of ferrets with fever between PBS and 100% horseradish treatment (>2SD rise in temperature from baseline)

| | | Group Number | | |
|---|---|---|---|---|
| | | PBS | 100% horseradish | Total |
| Fever => 2SD rise from baseline | No Count | 1 | 6 | 5 |
| | Expected count | 2.5 | 2.5 | 5.0 |
| | % within Group No. | 12.5% | 50% | 31.3% |
| | yes Count | 7 | 4 | 11 |
| | Expected count | 5.5 | 5.5 | 11.0 |
| | % within Group No. | 87.5% | 50% | 68.8% |
| Total | Count | 8 | 8 | 16 |
| | Expected count | 8.0 | 8.0 | 16.0 |
| | % within Group No. | 100% | 100% | 100% |

Chi-Squared Tests

| | Value | df | Asymp. Sig. (2-sided) | Exact Sig. (2-sided) | Exact Sig. (1-sided) |
|---|---|---|---|---|---|
| Pearson Chi-Square | 2.618[b] | 1 | .106 | | |
| Continuity Correction[a] | 1.164 | 1 | .281 | | |
| Likelihood Ration | 2.756 | 1 | .097 | | |
| Fisher's Exact Test | | | | .282 | .141 |
| Linear-by-Linear Association | 2.455 | 1 | .117 | | |
| N of Valid Cases | 16 | | | | |

[a]Computed only for 2 × 2 table
[b]2 cells (50.0%) have expected count less than 5. The maximum expected count is 2.50.

TABLE 54

$X^2$ analysis of the number of ferrets with fever between PBS and Tamiflu ™ treatment (>2SD rise in temperature from baseline)

| | | Group Number | | |
|---|---|---|---|---|
| | | PBS | Tamiflu ™ | Total |
| Fever => 2SD rise from baseline | No Count | 1 | 4 | 5 |
| | Expected count | 2.5 | 2.5 | 5.0 |
| | % within Group No. | 12.5% | 50% | 31.3% |
| | yes Count | 7 | 4 | 11 |
| | Expected count | 5.5 | 5.5 | 11.0 |
| | % within Group No. | 87.5% | 50% | 68.8% |
| Total | Count | 8 | 8 | 16 |
| | Expected count | 8.0 | 8.0 | 16.0 |
| | % within Group No. | 100% | 100% | 100% |

Chi-Squared Tests

| | Value | df | Asymp. Sig. (2-sided) | Exact Sig. (2-sided) | Exact Sig. (1-sided) |
|---|---|---|---|---|---|
| Pearson Chi-Square | 2.618[b] | 1 | .106 | | |
| Continuity Correction[a] | 1.164 | 1 | .281 | | |
| Likelihood Ration | 2.756 | 1 | .097 | | |
| Fisher's Exact Test | | | | .282 | .141 |
| Linear-by-Linear Association | 2.455 | 1 | .117 | | |
| N of Valid Cases | 16 | | | | |

[a]Computed only for 2 × 2 table
[b]2 cells (50.0%) have expected count less than 5. The maximum expected count is 2.50.

Conclusions

While all test substance treated ferrets seroconverted, QR-435 with 100% and 50% horseradish components were found to either significantly or nearly significantly, reduce the systemic illness as measured by weight and temperature. However, the other clinical signs of illness were not abrogated by any treatment. The control groups displayed clinical signs of influenza illness. The PBS treated groups exhibit the typical signs of influenza infection: weight loss, fever, and seroconversion as well as low clinical signs of illness, reduced activity and nasal signs. The Tamiflu™ treated groups show no significant weight loss, low clinical signs, virus shedding, reduced severity of fever and no seroconversion.

In the test treatment groups, the severity of illness was defined by fever and weight loss. All treatment dosages significantly reduced the severity of weight loss when compared to the PBS group. When fever was defined as a 2SD rise in temperature, the 50% horseradish treatment group showed significant reductions in the incidence of fever. The 100% horseradish treatment group also abrogated fever and was found to be nearly as significant. When fever was defined as a 3 SD rise in temperature, the 100% and 50% horseradish treatment groups had nearly significant reductions in the incidence of fever, but the 25% horseradish treatment did not abrogate fever. Thus, the 100% and the 50% horseradish treatments were found to reduce systemic signs to a greater degree than the 25% horseradish treatment. This suggests a strong dose dependency requiring 50% or greater horseradish to abrogate both fever and weight loss. Treatment with 50% or greater horseradish may reduce the titer of virus transmitted from the donor to the recipient thereby reducing the severity of disease symptoms. It is also possible that treatment with 50% or greater horseradish abrogated illness by acting in a therapeutic manner.

EXAMPLE 13

The first documented case of a human infection with an avian strain was the 1997 Hong Kong H5N1 infection of 18 persons resulting in 6 deaths. A more recent outbreak has occurred in Southeast Asia resulting in numerous deaths as shown in Table 55.

TABLE 55

Confirmed Human H5N1 (Avian) Influenza Cases in SE Asia (WHO 2004)

| Country | Total No. of cases | No. of Deaths |
|---|---|---|
| Vietnam | 22 | 15 |
| Thailand | 12 | 8 |
| Total | 34 | 23 |

This study investigated the efficacy of the formulations given in Tables 56–57 below, against a human isolate of an avian strain influenza virus A/Vietnam/1194/04, H5N1. The negative control was DMEM-DMSO 1% while the positive control in the virustatic assay was amatadine at 0.37 μM. The positive control for the virucidal assay was 1% Tween-20/20% ETOH/PBS (final concentration). In addition, cell only and virus only positive controls where used. The cell only control used maintenance media only. For the virus only control, the test procedures were identical except cell maintenance media was used instead of the test compounds. Tables 56–57 display the formulations that were tested.

TABLE 56

Formula I

| Ingredient | Weight % |
|---|---|
| Oleoresin Tumeric, ex. Kalsec | 0.6466 |
| Aquaresin Ginger, ex. Kalsec. | 0.6840 |
| Horseradish - Horseradish oil, ex. Kalsec | 0.06312 |
| Green Tea PE - 90% Phytoway Green Tea PE 030725. Huizhen S09160304 | 0.4619 |
| Glycerin | 49.0723 |
| Water | 49.0723 |
| TOTAL | 100.0002 |

TABLE 57

Formula II

| Ingredient | Weight % |
|---|---|
| Tumeric Extract in Vegetable Oil. Ex. Kalsec | 0.6466 |
| Oleoresin Ginger. Ex. Kalsec. | 0.6840 |
| Horseradish - Horseradish oil, ex. Kalsec | 0.06312 |
| Green Tea PE - 90% Phytoway Green Tea PE 030725. Huizhen S09160304 | 0.4619 |
| Glycerin | 36.9077 |
| Water | 36.9077 |
| Neobee M-5 Medium Chain Triglyceride | 12.2850 |
| BASF T-Maz Polysorbate 80K | 12.0441 |
| TOTAL | 100.0001 |

The end point of the virucidal assay was determined by visual observation of the cytopathic effects (CPE) and the residual viral titer was determined by the Karber method. Reduction of the virus titer exposed to the test compounds was determined by comparison to the virus only control. Antiviral activity is a reduction of $1-\log_{10} TCID_{50}/ml$ (See, Oxford, J. S., et al., "Sodium deoxycholate exerts a direct destructive effect on HIV and Influenza viruses in-vitro and inhibits retrovirus-induced pathology in an animal model." Antiv. Chem. Chemother., 5(3):176–181 (1994)). The end point of the virustatic assay was also determined by visual CPE scores. The antiviral activity was represented by the presence or absence of infection.

Virustatic Assay

In the virustatic assay both formulations I–II were diluted 1/10 ($10^1$), 1/100 ($10^2$) and 1/1000 ($10^3$). Additionally, undiluted formulations I–II ($10^0$) were tested. In the virustatic assay, Mardin-Darby canine kidney (MDCK) cells were seeded into 96-well plates (100 μl/well) and incubated for 2 days at 37° C. with 5% $CO_2$. After 2 days, the cells were washed two times with 100 μl/well PBS then exposed to 100 μl/well infection media. A $1/10^3$ dilution of neat viral stock was added to the cells and allowed to attach for 1 to 2 hours under standard incubator conditions (i.e. 37° C. with 5% $CO_2$). Each test formulation (diluted and undiluted) was then added to the infected wells at 50 μl/well. The plates were incubated for 3 days under standard incubator conditions. CPE observation and crystal violet staining determined the end point of the assay. Additionally, a hemagglutination assay (HA) was performed following a 2-fold dilution series.

Under crystal violet staining, some virustatic activity was observed when formulation I was used undiluted and for the $1/10^1$ dilution. The effective concentration, $EC_{50}$ was calculated to be $1/10^{1.88}$ (i.e. a dilution between $1/10^1$ and $1/10^2$).

In this assay, CPE was observed in all test wells for all dilutions of formulation II. Under crystal violet staining, no virustatic activity was observed with formulation II.

Table 58 displays the HA assay data from the virustatic assay.

TABLE 58

Virustatic Assay Activity

| | HA Titer (HAU) | |
|---|---|---|
| Dilution ($10^X$) | Formulation I | New Formulation II |
| 0 | 64 | <2* |
| −1 | 32 | <2* |
| −2 | 256 | 128 |
| −3 | 256 | 256 |

*The HAU (HA Units) value recorded here is likely to be due to the toxicity of the compound rather than the antiviral activity.

The HA titer for amatadine ranged from 16 to 32 HAU indicating little activity against the A/Vietnam/1194/04 strain.

Virucidal Assay

In the virucidal assay both Formulation I and II were diluted 1/10 and 1/80. In the virucidal assay, Mardin-Darby canine kidney (MDCK) cells were seeded into 96-well plates (100 μl/well) and incubated for 2 days at 37° C. with 5% $CO_2$. After 2 days, the cells were washed two times with 100 μl/well PBS then exposed to 100 μl/well infection media. A 1/1000 dilution of neat viral stock (40 μl/well) was added each test compound (360 μl) and left to incubate at room temperature for either 30 seconds or 5 minutes. The reaction was terminated by the addition of the infection media (3.6 ml). Termination of the reaction was caused by the 1:10 dilution. The termination mixture was added in duplicate (111 μl) to the first row of the 96 well plates and titrated across the plate following a 10-fold dilution series. The plates were incubated for 3 days under standard incubator conditions and CPE scored. A hemagglutionation assay (HA) was performed following a 2-fold dilution series.

Table 59 displays the HA data from the virucidal assay using formulation.

TABLE 59

Virucidal Activity of Formulation I

| | Formulation I (HAU) | | | |
|---|---|---|---|---|
| | 1/10 | | 1/80 | |
| | Time (minutes) | | | |
| Dilution ($10^x$) | 0.5 | 5 | 0.5 | 5 |
| 0 | <2 | <2 | 64 | <2 |
| −1 | <2 | <2 | <2 | <2 |
| −2 | <2 | <2 | <2 | <2 |
| −3 | <2 | <2 | <2 | <2 |
| −4 | <2 | <2 | <2 | <2 |
| Cell control | <2 | <2 | <2 | <2 |
| Virus control | 64 | 64 | 64 | 32 |

The data indicates that there is virucidal activity for formulation I after a 5 minute incubation and for the 1/10 dilution only after a 30 second incubation.

Table 60 displays HA data from the virucidal assay using formulation II.

TABLE 60

Virucidal Activity of Formulation II

| | Formulation II (HAU) | | | |
|---|---|---|---|---|
| | 1/10 | | 1/80 | |
| | Time (minutes) | | | |
| Dilution ($10^x$) | 0.5 | 5 | 0.5 | 5 |
| 0 | 256 | 256 | 32 | 256 |
| −1 | <2 | <2 | 16 | 32 |
| −2 | <2 | <2 | <2 | <2 |
| −3 | <2 | <2 | <2 | <2 |
| −4 | <2 | <2 | <2 | <2 |
| Cell control | <2 | <2 | <2 | <2 |
| Virus control | 32 | 64 | 64 | 64 |

Table 60 shows that there is some detectible virucidal activity with formulation II but reduced quantitatively when compared to that observed for formulation I. The positive control for both virucidal assays was 1% Tween-20/20% ETOH/PBS. The positive control had a <2 HAU consistently on all plates thus demonstrating good antiviral activity against the A/Vietnam/1194/04 strain.

Conclusion

Formulation I had detectable antiviral activity when tested in a virustatic assay. The activity was classified as moderate with approximately a 10-fold reduction in virus replication. However, some nonspecific changes were observed in the cell monolayer when incubated with the QR formulations, hence the precise contribution of the anticellular versus antiviral effects could not be quantified. Certain novel antivirals have been designated to exert viral inhibiting activity via an effect on cellular function. It is possible that the different components of the QR mixture are exerting different anticellular and antiviral effects.

Virucidal activity was detected in formulation II but formulation II had a lower efficacy than formulation I. One possible future study could be to investigate the contribution of each constituent of the complete compound.

To date NI (neuramidase inhibitor) blockers have been shown to inhibit the avian influenza strain H5N1, whereas amantadine has been shown to be relatively inactive against avian H5N1 strains.

It is to be understood, however, that even though numerous characteristics and advantages of the present invention have been set forth in the foregoing description, they are illustrative only. Changes may be made in carrying out the methods and to the compositions of the invention above set forth above without departing from the spirit and scope of the invention. It is intended that all matter contained in the above description shall be interpreted as illustrative and not in a limiting sense. The scope of this invention is to be determined from the claims appended hereto.

What is claimed is:

1. A method for reducing the transmissivity of a virus, comprising the step of administering to a mammal or a bird that has been exposed to an illness caused by a virus or has contracted an illness caused by a virus, a safe and effective amount of composition comprising:
   a first ingredient selected from the group consisting of ginger powder extract, ginger fluid extract, ginger powder, at least a part of a whole plant of ginger, a ginger tincture, and mixtures thereof;
   a second ingredient selected from the group consisting of green tea powder, green tea powder extract, green tea fluid extract, at least a part of a whole plant of green tea, tinctures of green tea, and mixtures thereof;
   an acceptable carrier;
   said amount being effective, when administered, to reduce an incidence of contracting said illness by another mammal or bird exposed to said mammal or bird relative to an incidence of contracting said illness by a mammal or bird exposed to a mammal or bird to which the composition has not been administered.

2. The method of claim 1, wherein said illness is caused by a virus selected from the group consisting of: herpes virus and an influenza virus.

3. The method of claim 2, wherein the virus is an influenza virus.

4. The method of claim 1, wherein the composition is administered in a form selected from a group consisting of a tablet, a capsule, a lozenge, a troche, a hard candy, a chewable composition, and a dental product.

5. The method of claim 1, wherein the composition is administered as a nasal spray or as a throat spray.

6. The method of claim 1, wherein the first ingredient comprises ginger root powder and the second ingredient comprises green tea extract.

7. The method of claim 1, wherein each gram of the composition contains about 1 mg to about 20 mg of green tea extract, and about 1 mg to about 150 mg of ginger root powder.

8. The method of claim 1, wherein the composition further comprises a third ingredient selected from thea group consisting of turmeric powder extract, turmeric fluid extract, turmeric extract, curcuminoids, turmeric powder, at least a part of a whole plant of turmeric, a turmeric tincture, and mixtures thereof.

9. The method of claim 8, wherein the third ingredient comprises turmeric extract.

10. The method of claim 6, wherein the third ingredient comprises turmeric extract.

11. The method of claim 8, wherein the composition contains about 1 mg to about 20 mg of turmeric powder extract.

12. The method of claim 8, wherein the composition further comprises a fourth ingredient selected from the group consisting of horseradish root and horseradish extract.

13. The method of claim 1, wherein the composition further comprises one or more ingredients selected from the group consisting of ethanol, resveratrol, propylene glycol and glycerine.

14. The method of claim 13, wherein the composition comprises ethanol.

15. A method for the prophylactic use of a composition to reduce one or more of severity of a viral illness, severity of symptoms of the viral illness, and incidence of symptoms of the viral illness, comprising the step of administering to a mammal or a bird that has been, or will be, exposed to the viral illness, an amount of a composition comprising:
- a first ingredient selected from the group consisting of ginger powder extract, ginger fluid extract, ginger powder, at least a part of a whole plant of ginger, a ginger tincture, and mixtures thereof;
- a second ingredient selected from the group consisting of green tea powder, green tea powder extract, green tea fluid extract, at least a part of a whole plant of green tea, tinctures of green tea, and mixtures thereof;
- an acceptable carrier;
- said amount being effective, when administered, to reduce one or more of the severity of the viral illness, the severity of symptoms of the viral illness, and the incidence of symptoms of the viral illness relative to a mammal or bird to which the composition has not been administered.

16. The method of claim 15, wherein said illness is caused by a virus from selected from the group consisting of: a herpes virus and an influenza virus.

17. The method of claim 16, wherein the virus is an influenza virus.

18. The method of claim 15, wherein the composition is administered in a form selected from a group consisting of a tablet, a capsule, a lozenge, a troche, a hard candy, a chewable composition, and a dental product.

19. The method of claim 15, wherein the composition is administered as a nasal spray or as a throat spray.

20. The method of claim 15, wherein the first ingredient comprises ginger root powder and the second ingredient comprises green tea extract.

21. The method of claim 15, wherein each gram of the composition contains about 1 mg to about 20 mg of green tea extract, and about 5 mg to about 150 mg of ginger root powder.

22. The method of claim 15, wherein the composition further comprises a third ingredient selected from the group consisting of turmeric powder extract, turmeric fluid extract, turmeric extract, curcuminoids, turmeric powder, at least a part of a whole plant of turmeric, a turmeric tincture, and mixtures thereof.

23. The method of claim 22, wherein the third ingredient comprises turmeric extract.

24. The method of claim 20, wherein the third ingredient comprises turmeric extract.

25. The method of claim 22, wherein the composition contains about 1 mg to about 20 mg of turmeric powder extract.

26. The method of claim 15, wherein the composition further comprises a fourth ingredient selected from the group consisting of horseradish root and horseradish extract.

27. The method of claim 15, wherein the composition further comprises one or more ingredients selected from the group consisting of ethanol, resveratrol, propylene glycol and glycerine.

28. The method of claim 27, wherein the composition comprises ethanol.

29. The method of claim 10, wherein the composition further comprises a fourth ingredient selected from the group consisting of horseradish root, horseradish oil and horseradish flavor.

30. The method of claim 24, wherein the composition further comprises a fourth ingredient selected from the group consisting of horseradish root, horseradish oil and horseradish flavor.

* * * * *